United States Patent
O'Leary et al.

(10) Patent No.: US 11,737,923 B2
(45) Date of Patent: Aug. 29, 2023

(54) APPARATUS AND METHODS FOR EAR PROTECTION AND ENHANCEMENT

(71) Applicant: MDIDEAFACTORY, INC., San Diego, CA (US)

(72) Inventors: Michael J. O'Leary, Del Mar, CA (US); Daniel Joseph Braun, San Diego, CA (US); Randy Wayland, San Diego, CA (US); Robert F. Gazdzinski, San Diego, CA (US)

(73) Assignee: MDIDEAFACTORY, INC., San Diego, CA (US)

( * ) Notice: Subject to any disclaimer, the term of this patent is extended or adjusted under 35 U.S.C. 154(b) by 749 days.

(21) Appl. No.: 16/780,661

(22) Filed: Feb. 3, 2020

(65) Prior Publication Data
US 2020/0253784 A1      Aug. 13, 2020

Related U.S. Application Data

(63) Continuation of application No. 15/478,130, filed on Apr. 3, 2017, now abandoned.
(Continued)

(51) Int. Cl.
*A61F 11/08*      (2006.01)
*H04R 25/00*      (2006.01)

(52) U.S. Cl.
CPC ............ *A61F 11/08* (2013.01); *H04R 25/604* (2013.01); *A61F 11/085* (2022.01); *A61F 2250/0004* (2013.01); *A61F 2250/0075* (2013.01)

(58) Field of Classification Search
CPC ........ A61F 11/06; A61F 11/08; A61F 11/085; A61F 11/145; A61F 2250/0004; A61F 2250/0075; H04R 25/604
See application file for complete search history.

(56) References Cited

U.S. PATENT DOCUMENTS

| | | | |
|---|---|---|---|
| 4,244,377 A | 1/1981 | Grams | |
| 4,408,605 A | 10/1983 | Doerr | |

(Continued)

FOREIGN PATENT DOCUMENTS

| | | |
|---|---|---|
| CN | 204971851 U | 1/2016 |
| WO | WO-2009086649 A1 | 7/2009 |
| WO | WO-2015160196 A1 | 10/2015 |

OTHER PUBLICATIONS

"Geckskin", UMassAmherst, The College of Natural Sciences, retrieved from the Internet: https://geckskin.umass.edu/ on Jul. 3, 2017, 10 pages.

(Continued)

*Primary Examiner* — Keri J Nelson
(74) *Attorney, Agent, or Firm* — Patent Beach PC

(57) ABSTRACT

Apparatus for protection of the ear and ear canal, and related methods of use and operation. In one embodiment, the apparatus includes a selectively actuated valve which permits a varying or modulated size of aperture to be created by the wearer while the apparatus is in use, so as to accommodate varying functions, such as complete occlusion (e.g., for use in swimming or other aquatic activities such that water can be completely excluded) or partial occlusion (e.g., such that sounds can be heard by the wearer, whether in air or under water). In one implementation, the apparatus is retained within the ear canal of the wearer by virtue of the apparatus' shape and coordination with one or more natural features or contours of the anatomy in the ear region, without having to be inserted more than superficially into the outer portion of the ear canal.

20 Claims, 18 Drawing Sheets

Related U.S. Application Data

(60) Provisional application No. 62/318,106, filed on Apr. 4, 2016.

(56) References Cited

U.S. PATENT DOCUMENTS

| | | | |
|---|---|---|---|
| 5,692,059 | A | 11/1997 | Kruger |
| 5,755,681 | A | 5/1998 | Plews |
| 6,082,485 | A | 7/2000 | Smith |
| 6,257,235 | B1 | 7/2001 | Bowen |
| 6,354,296 | B1 | 3/2002 | Baumann et al. |
| 6,543,450 | B1 | 4/2003 | Flynn |
| 7,766,015 | B2 | 8/2010 | Harold et al. |
| 9,088,846 | B2 * | 7/2015 | Blanchard ............ H04R 1/1016 |
| 2003/0116165 | A1 | 6/2003 | Huang |
| 2003/0195588 | A1 | 10/2003 | Fischell et al. |
| 2008/0066209 | A1 | 3/2008 | Kayerod |
| 2011/0066172 | A1 | 3/2011 | Silverstein |
| 2011/0158421 | A1 | 6/2011 | Voix et al. |
| 2012/0318605 | A1 | 12/2012 | Brown et al. |
| 2013/0180529 | A1 | 7/2013 | Matich |
| 2013/0247669 | A1 | 9/2013 | Swanson et al. |
| 2013/0296987 | A1 | 11/2013 | Rogers et al. |
| 2014/0062567 | A1 | 3/2014 | Waters et al. |
| 2014/0206947 | A1 | 7/2014 | Isserow et al. |
| 2014/0249608 | A1 | 9/2014 | Rogers |
| 2014/0270257 | A1 * | 9/2014 | Bauman .................. A61F 11/08 381/109 |
| 2015/0005793 | A1 | 1/2015 | Collins et al. |
| 2015/0142029 | A1 | 5/2015 | Fahn et al. |
| 2015/0320591 | A1 | 11/2015 | Smith et al. |
| 2016/0008176 | A1 | 1/2016 | Goldstein |
| 2016/0015098 | A1 | 1/2016 | Conlon |
| 2017/0135854 | A1 | 5/2017 | Rogers et al. |
| 2017/0281416 | A1 | 10/2017 | O'Leary et al. |
| 2019/0001117 | A1 | 1/2019 | Ben-David et al. |

OTHER PUBLICATIONS

"Ultrathin Rechargeable Lithium Polymer Batteries from Powerstream," Powerstream, Jun. 29, 2017, retrieved from the Internet: https://www.powerstream.com/thin-lithium-ion.htm on Jul. 3, 2017, 4 pages.
Barros A.C., et al., "From Nystagmus to the Air and Water Caloric Tests," Brazilian Journal of Otorhinolaryngology, 2012, vol. 78 (4), pp. 120-125.
Behavior Therapy in Psychiatry, Task Force Report 5. Washington, D.C, American Psychiatric Association, 1973, 87 pages.
Bernstein I.L., "Food Aversion Learning: A Risk Factor for Nutritional Problems in the Elderly?," Physiology & Behavior, 1999, vol. 66 (2), pp. 199-201.
Bush M.L., et al., "Hot or cold? Is Monothermal Caloric Testing Useful and Cost-effective?," The Annals of Otology, Rhinology, and Laryngology, 2013, vol. 122 (6), pp. 412-416.
Cunha L.C., et al., "Validity of the Monothermal Caloric Testing When Compared to Bithermal Stimulation," Pro Fono., 2010, vol. 22 (1), pp. 67-70.
Elkins R.L., "Conditioned Flavor Aversions to Familiar Tap Water in Rats: An Adjustment With Implications for Aversion Therapy Treatment of Alcoholism and Obesity," Journal of Abnormal Psychology, 1974, vol. 83 (4), pp. 411-417.
Health Technology Case Study 22, The Effectiveness and Costs of Alcoholism Treatment, Research on the Effectiveness of Alcoholism Treatment, Jul. 1973, pp. 43-53.
Knibb R.C., et al., "No Unique Role for Nausea Attributed to Eating a Food in the Recalled Acquisition of Sensory Aversion for That Food," Appetite, 2001, vol. 36 (3), pp. 225-234.
Melagrana A., et al., "Comparison Between Air and Water Caloric Tests in Children," International Journal of Pediatric Otorhinolaryngology, 1999, vol. 51 (3), pp. 139-143.
Proctor L.R., "Clinical Experience With a Short-acting Caloric Test," Laryngoscope, 1985, vol. 95 (1), pp. 75-80.
Walther L.E., et al., "Caloric Stimulation With Near Infrared Radiation Does Not Induce Paradoxical Nystagmus," Acta otorhinolaryngologica Italica, 2011, vol. 31 (2), pp. 90-95.

* cited by examiner

APPARATUS AND METHODS FOR EAR PROTECTION AND ENHANCEMENT

PRIORITY

This application is a continuation of and claims priority to co-pending U.S. patent application Ser. No. 15/478,130 of the same title filed Apr. 3, 2017, which claims priority to U.S. Provisional Patent Application Ser. No. 62/318,106 filed Apr. 4, 2016, of the same title, each of the foregoing which is incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

1. Technological Field

The disclosure relates to apparatus and methods for protecting and selectively utilizing the inner ear and ear canal of a living being (such as a human), and in one exemplary aspect to an ear "plug" for use in humans that is comfortable to wear for extended periods, effectively seals to the wearer's anatomy around its periphery, can be selectively actuated or modulated so as to vary a degree of isolation between the exterior of the plug and the interior thereof (i.e., disposed within the ear canal), such as to selectively admit or exclude air, sound, and/or water therefrom.

2. Description of Related Technology

Hearing protection apparatus are well known in the prior art. Such hearing protection apparatus include for example exterior headsets or the like which include "cups" that cover the entirety of the exterior portions of the wearer's ears, in effect forming a barrier between sound (and other impinging energy or substances) and the anatomy of the ear. See FIG. 1. Such apparatus are typically uncomfortable, obstructive and bulky, and not well suited to any environment other than air (e.g., are not sealed against water intrusion). Moreover, they are not selectively actuated by the wearer such that they can selectively admit or exclude sound (e.g., to hear someone speaking during periods of relative quiet); rather, the wearer must remove one or both of the cups to expose the ear to the ambient environment. In a very loud environment that is intermittent or unpredictable in nature, this can also represent a hazard; e.g., at a firearms shooting range, removing one or both cups from a user's ear so that they can conduct a conversation, exposes the ear to potential trauma from unexpected discharges from others at the range.

Other types of hearing protection are known, and include e.g., so-called "ear plugs". Ear plugs span a wide range of different configurations and materials, but all generally share the characteristic that they are received within the wearer's ear canal and retained therein (e.g., frictionally, and/or by an external biasing mechanisms such as a sprung metal or plastic loop that in essence forces each plug into its respective ear canal). The aforementioned "frictional" retention schemes take many different forms, including e.g., by virtue of (i) shape (e.g., such that they "catch" on the interior surfaces of the ear canal); and/or (ii) elastomeric or similar resilience (e.g., they are compressed before insertion, and then subsequently expand in the ear canal to create friction against the walls of the ear canal). FIGS. 2 and 3 herein illustrate examples of such prior art ear plugs.

While widely used, such ear plugs may suffer from one or more of several deficiencies, including the requirement for positioning too far into the ear canal which produces discomfort, such as due to the creation of pressure on the tissue and bone of the inner ear. Specifically, some prior art ear plugs (e.g., of the compressible foam variety; see FIG. 4) require a significant outward bias pressure against the sensitive inner surfaces of the ear canal (and bone thereunder) to maintain the plugs in place, thereby leading to significant discomfort for the wearer even after comparatively short periods of time.

Moreover, many such ear plug configurations have no mechanism to selectively allow passage of sound, etc. through the plug, or such mechanisms are unwieldy. For instance, the prior art plugs of FIG. 5 (Surefire® Earpro "Sonic Defenders") utilize a system wherein loud sounds are ostensibly blocked, while those of lower volume (e.g., below 80 db) are permitted to pass. When more complete isolation is desired, the user then inserts "stopper plugs" into the main plug, thereby ostensibly blocking sounds below 80 db. However, the stopper plugs require the user to locate them by feel (they are in the illustrated device captured around the neck of the aperture in which they fit), and in effect "find the hole" to insert them via trial and error. Moreover, as with the other prior art plugs, those of FIG. 5 require deep insertion within the ear canal, using a series (three) of progressively smaller diameter rounded conic shapes as shown. As noted supra, such deep insertion is undesirable in that it, inter alia, can result in discomfort for the wearer.

Exostoses and Other Conditions

Notwithstanding the foregoing variety of ear plugs and hearing protection, there is also a salient need for protection against (or at very least mitigation of) various forms of exostosis; e.g., physiological processes wherein formation of new bone occurs on e.g., the cortical surface of the ear canal bone, most commonly stimulated by the exposure of the canal to cold water or air. The condition occurs frequently in those exposed to comparatively cold air or water on a regular basis; e.g., surfers, scuba divers, mountaineers, those living in routinely cold climates, etc. Specifically, as shown in FIGS. 6A and 6B, over time and with exposure to the cold water or air, the ear canal becomes progressively narrower, which can result in a host of issues including, inter alia, (i) reduced hearing in the affected ear(s); (ii) pain/discomfort; and (iii) obstruction due to buildup of ear wax. This condition can become quite severe in advanced stages; see FIG. 7A (showing a "before" image of an normal ear canal with no diminution in diameter, the white annulus marking periphery of tympanic membrane), and FIG. 7B (showing an "after" image of the same canal with advanced exostosis, and complete occlusion of the ear canal). It is also generally accepted that there is a genetic component to exostoses; i.e., persons stemming from certain regions and genetic lineage are more susceptible than others to such condition(s).

Another major part of the reason that exostosis develops in the foregoing subset of the general population is that such groups require the ability to hear while participating in their respective activities. For example, surfers who frequent the typically cold waters off California coastal areas are often surfing with several others in immediate proximity; the ability to hear warnings or "alters" can be an critical safety issue for both parties (and others). Being hit with a moving surfboard due to unawareness of others can be fatal. However, the need for such hearing capability is not uniform during the totality of the surfer's time in the water; for example, once the surfer "catches his/her wave", the likelihood for exposure of the ears to cold water increases (e.g., when they fall off their board), and the need for hearing others is obviated.

Accordingly, surfers typically opt for no ear protection (e.g., plugs) rather than being left with no hearing capability, or having to constantly insert/remove such plugs while surfing (the latter which is largely untenable). This complete failure to occlude the ear canal can lead to exposure to the cold water for extended periods of time, which leads to exostosis. This becomes particularly acute if the surfer stays out for many hours, and/or surfs frequently (e.g., several times per week). Some surfers do wear wetsuit hoods (e.g., hoods made of neoprene or other elastomeric materials that cover significant portions of the surfer's head, including the ears), but such hoods none-the-less typically allow for flow of ambient temperature water (or slightly warmer, due to the insulating layer of water between the wearer's skin and the hood interior surface) into the ear canal, and also disadvantageously block at least some sound, thereby impairing the surfer's hearing. Such hoods can also be uncomfortable to wear for extended periods. Hence, these hoods are not an optimal solution.

Similarly, persons with other conditions such as a compromised ear drum (e.g., ruptured due to mechanical injury or trauma), irritated or infected ear canal, may have need of at least partly blocking the ear canal for a period of time. However, such blockage can lead to discomfort due to irritation of the tissue on the interior surfaces of the canal, bacterial growth due to, inter alia, lack of air circulation, and other undesirable side-effects, as well as the loss of hearing ability in the affected ear(s) while obstructed. Completely and indiscriminately blocking off the ear canal in such cases is clearly not optimized for wearer healing, recovery and comfort.

In addition to the foregoing, there are other applications where it is desirable to effectively yet selectively occlude the ear canal, whether in an air-filled or aquatic environment, so as to e.g., protect one's hearing for extended periods of time, and/or stave off other deleterious effects of exposure to that environment. For instance, harmful airborne or impinging external influences such as e.g., sparks from welding, airborne radioactive contamination (such as within commercial or government nuclear plants or laboratories), or other such hazards should be excluded from the ear canal of a user.

Hence, based on the foregoing, what is needed is a comfortable and effective apparatus which can be used or adapted for use in a variety of different environments, and which can provide easy selection by the user of two or more levels of sound, air and/or water flow attenuation.

SUMMARY

The present disclosure addresses the foregoing needs by providing, inter alia, an improved apparatus and methods for ear and ear canal protection.

In a first aspect of the disclosure, a selectively operable or actuated ear occlusion apparatus is described. In one embodiment, the apparatus includes an ear plug having a valve assembly therein which permits modulation of an amount of air, water, and/or sound that enters the ear canal from an exterior environment.

In one variant, the valve assembly is accessible to and manually operable by the wearer with e.g., a tip of one finger. In one implementation, the valve assembly comprises a substantially planar element disposed at least partly on an exterior surface of the body of the ear plug, and is configured such that a wearer of the apparatus can actuate the valve via rotation of the substantially planar element around an axis, the axis disposed substantially perpendicular to a plane of the planar element.

In another variant, the valve assembly is selectively (and passively) actuated or de-actuated via a thermally reactive material within at least a portion of the plug body.

In another variant, the plug is designed to cooperate with one or more anatomical features of the wearer such that it is retained within the ear canal with a minimum depth of insertion, and maximum degree of comfort. In one implementation, the one or more anatomical features include the tragus of the outer ear of a human being. In another implementation, the so-called "conchal Incisura" is utilized to assist in, inter alia, maintaining the desired orientation (including roll prevention), position, and lead-in for alignment during insertion.

In a further variant, the exterior material(s) of at least a portion of the outer plug body is configured to aid in retention of the ear plug within the outer ear canal. In one variant, the material comprises a plurality of synthetic "micro-setae" disposed on the outer surface of the plug body so as to enable the setae to interact with the surface of the dermis of the wearer's ear canal tissue, thereby largely obviating generally undesirable outward bias pressures which can lead to irritation of such sensitive tissues.

In yet a further variant, the plug is configured to be retained in place via an external mechanism (whether alone or in conjunction with the foregoing cooperation with the anatomical features of the wearer). In one implementation, the mechanism comprises a magnetic backing plate which interacts with a magnet of the ear plug through the tissue of the wearer.

In another implementation, the plug is configured to be retained at least partly via an internal mechanism of the plug; e.g., a circumferentially expanding ring or region which contacts a portion of the inner surface of the outer portion of the ear canal, and which can be selectively actuated by the wearer.

In a further implementation, the plug is configured to be retained at least partly via an internal mechanism of the plug; e.g., a circumferentially expanding ring or region which contacts a portion of the inner surface of the outer portion of the ear canal under interior spring assembly expansive force.

In yet a further implementation, the plug is sized and shaped so as to be retained generally in the desired place, but not provide a complete seal around its periphery with the surrounding ear tissue, seeking only to mitigate cold water or air flow into the ear canal, and not completely prevent it, thereby maximizing comfort for the wearer during periods of extended use.

In a second aspect, apparatus for mitigating or preventing exostosis in a living being are disclosed. In one embodiment, the apparatus comprises a set of ear plugs which allow the wearer to easily selectively modulate the amount of air/sound/water flow through the plugs and into the ear canal. In one variant, the apparatus is configured to be disposed in the outer portion of the ear canal, thereby obviating "deep" insertion into the canal, and protection of the maximal amount of the canal form exposure to e.g., cold air or water.

In a third aspect, a method of preventing or mitigating exostosis in a living being is disclosed. In one embodiment, the method includes selectively actuating a variable orifice within a plug apparatus disposed in the ear canal, so as to limit the flow of cold air or water into the ear canal.

In a further aspect, a method of treating a patient with an ear canal or ear drum condition or deficiency is disclosed. In one embodiment, the method includes installing a selectively variable aperture plug apparatus within the outer portion of the ear canal (e.g., so as to control the amount of sound, external contamination, or other deleterious substances or effects incident on the region); adjusting the variable aperture so as to permit a desired amount of air and sound there through during normal wear; and re-adjusting the aperture so as to exclude moisture during e.g., showering or other situations where substantial water or water vapor is present.

In a further aspect, a method of using an ear plug apparatus is disclosed.

In yet a further aspect, methods of installing and removing an ear plug apparatus are disclosed.

In another aspect, apparatus for mechanical retention of an earplug apparatus are disclosed. In one embodiment, the apparatus for retention comprises a substantially planar and curved structure with a magnetic element associated therewith; the magnetic element generates a magnetic field that at least partly permeates through the wearer's outer ear tissue to interact with a corresponding ferrous or other magnetized element within an ear plug assembly oriented so as to cause attraction between the two elements through the user's tissue, thereby retaining the ear plug assembly (and the planar curved structure) in a substantially constant orientation and position.

In another aspect, electronic apparatus is disclosed. In one embodiment, the electronic apparatus includes an at least partly compliant outer body, and an interior cavity configured to contain a plurality of electronic components. In one variant, the components include a Bluetooth transceiver, and a micro-acoustic assembly. The micro-acoustic assembly in one implementation comprises a small speaker and driving coil (and amplifier) akin to those used in "ear buds", yet with reduced audio power capabilities so as to obviate electrical cords. A micro (e.g., flat planar and flexible) lithium ion battery is included in the cavity to power the electronic components and audio output. The battery can be recharged inductively, thereby obviating exposed electrical terminals.

In another variant, the micro-acoustic assembly is configured to act as a transceiver; i.e., to operate as a speaker and vibrate an acoustic transducer under variations in voltage applied to the driving coil, and also act as a passive "microphone" to generate voltages via the coil when the transducer is vibrated by e.g., the wearer's voice while speaking (e.g., the placement of the transducer allows for bone conduction; e.g., where the wearer's jawbone meets the ear canal).

In another variant, the components include a Wi-Fi transceiver (e.g., Wi-Fi or Wi-Fi "Direct" enabled) that modulates its transmission power within the frequency band of interest to communicate only with very nearby Wi-Fi enabled devices (e.g., the user's smartphone or tablet when in their immediate possession or jacket pocket), so as to mitigate electromagnetic radiation (EMR) dose to the wearer when in use.

In a further variant, an IEEE Std. 802.15 PAN enabled integrated circuit device (e.g., Zigbee® or the like) is utilized within the cavity.

In another variant, the electronic apparatus is configured as a selectively actuated ear plug, and the plug(s) act as one or more "IoT" ("Internet of things") entities such that it can receive and/or transmit data of utility in various types of applications.

In another variant, the electronic apparatus is configured as a selectively actuated ear plug, and the plug(s) is configured to selectively turn on and off its transceiver (as well as other functions) as the valve is closed and opened, respectively.

In a further aspect, a reduced-profile selectively actuated ear apparatus is disclosed. In one embodiment, the apparatus comprises a body with a substantially cylindrical shape, and substantially planar ends generally normal to the axis of the cylindrical body. The plug body is configured to be received in the outer portion of the ear canal only, and sized to be retained by, inter alia, the tragus of the wearer's ear. The valve actuation mechanism is a substantially flat plate on the outer end of the plug body which the user can rotate with their finger tip. The flat plate gives the plug a low profile (as compared to e.g., the prior art plug of FIG. 5), and is aesthetically pleasing. The flat plate can also be configured to bear indicia, images, etc. (e.g., direction of rotation, corporate trademarks or logos, etc.), and/or be of prescribed colors or patterns.

Other features and advantages of the present disclosure will immediately be recognized by persons of ordinary skill in the art with reference to the attached drawings and detailed description of exemplary embodiments as given below.

Figure 1:
FIG. 1 is a front perspective view of one type of prior art hearing protection device.
Figure 2:
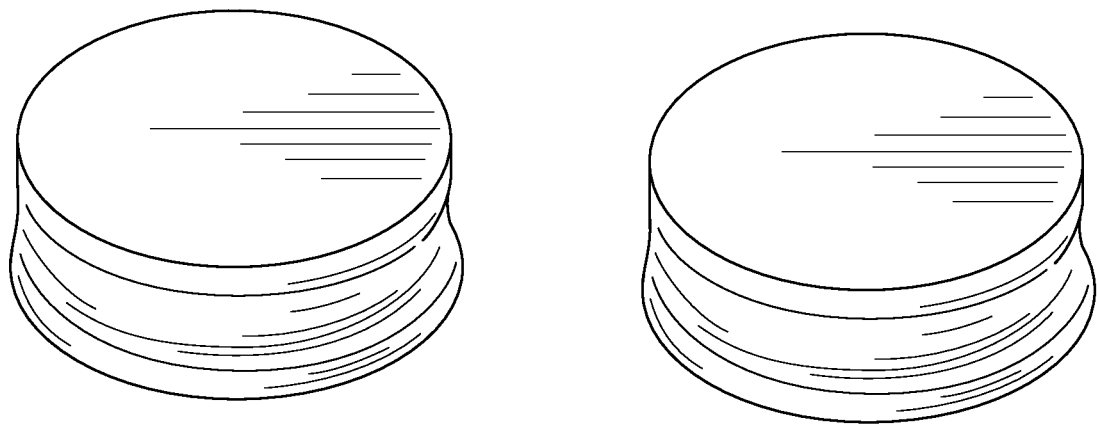
FIG. 2 is a perspective view of another type of prior art hearing protection device (i.e., "plug" type received within the wearer's ear canal(s)).
Figure 3:
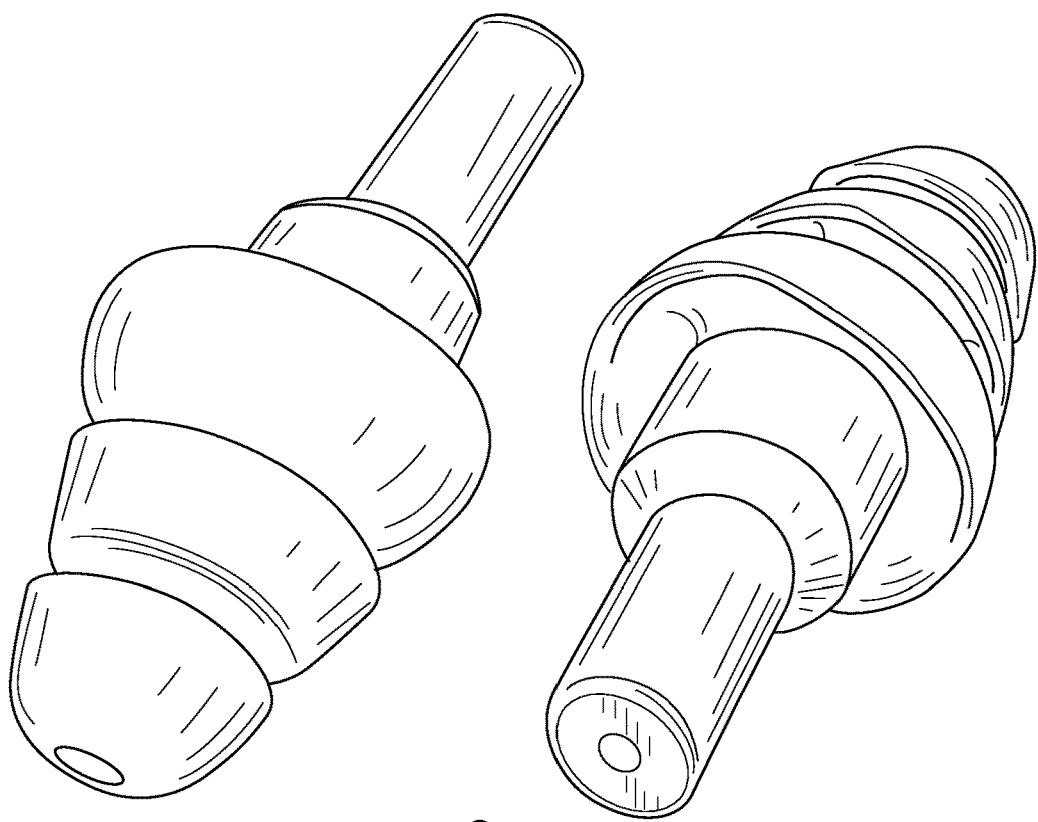
FIG. 3 is a perspective view of another variation of the "plug" type of protection device according to the prior art.
Figure 4:
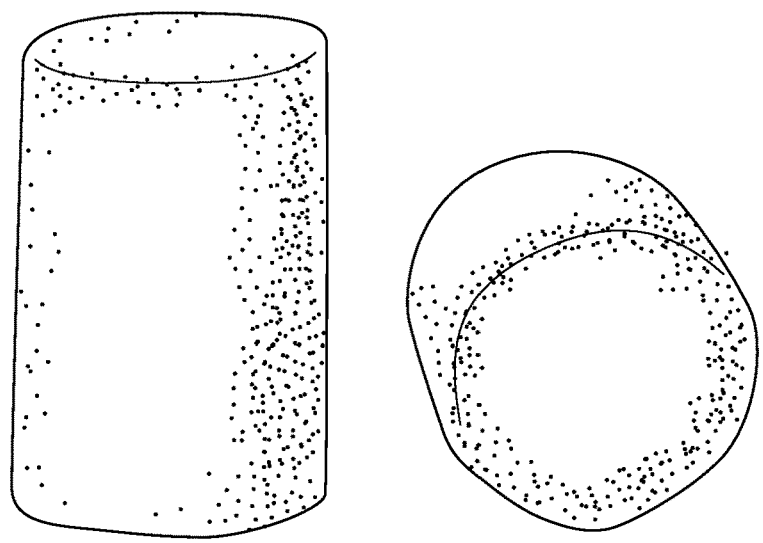
FIG. 4 is a perspective view of yet another variation of the "plug" type of protection device according to the prior art.

All figures © Copyright 2015-2016 MD Idea Factory. All rights reserved.

DESCRIPTION OF THE DISCLOSURE

Reference is now made to the drawings wherein like numerals refer to like parts throughout.

As used herein, the term "access point" refers generally and without limitation to a network node which enables communication between a user or client device and another entity within a network, such as for example a Wi-Fi AP, or a Wi-Fi-Direct enabled device acting as a Group Owner (GO).

As used herein, the term "application" refers generally and without limitation to a unit of executable software that implements a certain functionality or theme. The themes of applications vary broadly across any number of disciplines and functions (such as on-demand content management, e-commerce transactions, brokerage transactions, home entertainment, calculator etc.), and one application may have more than one theme. The unit of executable software generally runs in a predetermined environment; for example, the unit could include a downloadable Java Xlet™ that runs within the JavaTV™ environment.

As used herein, the term "client device" includes, but is not limited to, set-top boxes (e.g., DSTBs), gateways, modems, personal computers (PCs), and minicomputers, whether desktop, laptop, or otherwise, and mobile devices such as handheld computers, PDAs, personal media devices (PMDs), tablets, "phablets", smartphones, and vehicle infotainment or similar systems.

As used herein, the term "codec" refers to a video, audio, or other data coding and/or decoding algorithm, process or apparatus including, without limitation, those of the MPEG (e.g., MPEG-1, MPEG-2, MPEG-4/H.264, etc.), Real (RealVideo, etc.), AC-3 (audio), DiVX, XViD/ViDX, Windows Media Video (e.g., WMV 7, 8, 9, 10, or 11), ATI Video codec, or VC-1 (SMPTE standard 421M) families.

As used herein, the term "computer program" or "software" is meant to include any sequence or human or machine cognizable steps which perform a function. Such program may be rendered in virtually any programming language or environment including, for example, C/C++, Fortran, COBOL, PASCAL, assembly language, markup languages (e.g., HTML, SGML, XML, VoXML), and the like, as well as object-oriented environments such as Java™ (including J2ME, Java Beans, etc.) and the like.

As used herein, the terms "Internet" and "internet" are used interchangeably to refer to inter-networks including, without limitation, the Internet. Other common examples include but are not limited to: a network of external servers, "cloud" entities (such as memory or storage not local to a device, storage generally accessible at any time via a network connection, and the like), service nodes, access points, controller devices, client devices, etc.

As used herein, the term "memory" includes any type of integrated circuit or other storage device adapted for storing digital data including, without limitation, ROM. PROM, EEPROM, DRAM, SDRAM, DDR/2 SDRAM, EDO/FPMS, RLDRAM, SRAM, "flash" memory (e.g., NAND/NOR), and PSRAM.

As used herein, the terms "microprocessor" and "processor" or "digital processor" are meant generally to include all types of digital processing devices including, without limitation, digital signal processors (DSPs), reduced instruction set computers (RISC), general-purpose (CISC) processors, microprocessors, gate arrays (e.g., FPGAs), PLDs, reconfigurable computer fabrics (RCFs), array processors, secure microprocessors, and application-specific integrated circuits (ASICs). Such digital processors may be contained on a single unitary IC die, and/or distributed across multiple components.

As used herein, the term "network" refers generally to any type of telecommunications or data network including, without limitation, data networks (including MANs, WANs, LANs, WLANs, internets, and intranets). Such networks or portions thereof may utilize any one or more different topologies (e.g., ring, bus, star, loop, etc.), transmission media (e.g., wired/RF cable, RF wireless, millimeter wave, optical, etc.) and/or communications or networking protocols (e.g., SONET, DOCSIS, IEEE Std. 802.3, ATM, X.25, Frame Relay, 3GPP, 3GPP2, LTE, WAP, SIP, UDP, FTP, RTP/RTCP, H.323, etc.).

As used herein, the term "network interface" refers to any signal or data interface with a component or network including, without limitation, those of the IEEE-1394, USB (e.g., USB2), Ethernet (e.g., 10/100, 10/100/1000 (Gigabit Ethernet), 10-Gig-E, etc.), Wi-Fi (802.11), WiMAX (802.16), Zigbee®, Z-wave, PAN (e.g., 802.15, Bluetooth), power line carrier (PLC), or IrDA families.

As used herein, the term "shape memory alloy" or "SMA" shall be understood to include, but not be limited to, any metal that is capable of "remembering" or substantially reassuming a previous geometry. For example, after it is deformed, it can either substantially regain its original geometry by itself during e.g., heating (i.e., the "one-way effect") or, at higher ambient temperatures, simply during unloading (so-called "pseudo-elasticity"). Some examples of shape memory alloys include nickel-titanium ("NiTi" or "Nitinol") alloys and copper-zinc-aluminum alloys.

As used herein, the term "Wi-Fi" refers to, without limitation and as applicable, any of the variants of IEEE-Std. 802.11 or related standards including 802.11 a/b/g/n/s/v/ac or 802.11-2012/2013, as well as Wi-Fi Direct (including inter alia, the "Wi-Fi Peer-to-Peer (P2P) Specification", incorporated herein by reference in its entirety).

As used herein, the term "wireless" means any wireless signal, data, communication, or other interface including without limitation Wi-Fi, Bluetooth, 3G (3GPP/3GPP2), HSDPA/HSUPA, TDMA, CDMA (e.g., IS-95A, WCDMA, etc.), FHSS, DSSS, GSM, PAN/802.15, WiMAX (802.16), 802.20, Zigbee®, Z-wave, narrowband/FDMA, OFDM, PCS/DCS, LTE/LTE-A, analog cellular, CDPD, satellite systems, millimeter wave or microwave systems, acoustic, and infrared (i.e., IrDA).

Overview

Improved apparatus for protection of the ear and ear canal, and related methods of use and operation are disclosed herein. In one embodiment, the apparatus includes a selectively actuated valve which permits a varying or modulated size of aperture to be created by the wearer while the apparatus is in use, so as to accommodate varying functions, such as complete occlusion (e.g., for use in swimming or other aquatic activities such that water can be completely excluded from the ear canal) or partial occlusion (e.g., such that sounds can be heard by the wearer, whether in air or to under water).

In one implementation, the apparatus is oriented and retained within the ear canal of the wearer by virtue of the apparatus' shape and coordination with one or more natural features or contours of the anatomy in the ear region. A retention element is formed in the outer end of the apparatus, and cooperates with the surrounding cartilaginous anatomical features (including the wearer's tragus/"tragal valve" and conchal bowl (aka cavum concha)) to retain the apparatus in the desired location and orientation. The exemplary embodiment of the apparatus is purposely designed to avoid deep insertion into the ear canal (where as discussed above, many sources of discomfort for the wearer originate), thereby maintaining comfort for extended periods, as well as the desired level of occlusion for water, sound, air, contaminants, etc.

Anatomy

A brief discussion of the exemplary human ear anatomy is useful in further explanation of the various features and advantages of the apparatus and methods of the present disclosure.

Figure 8:
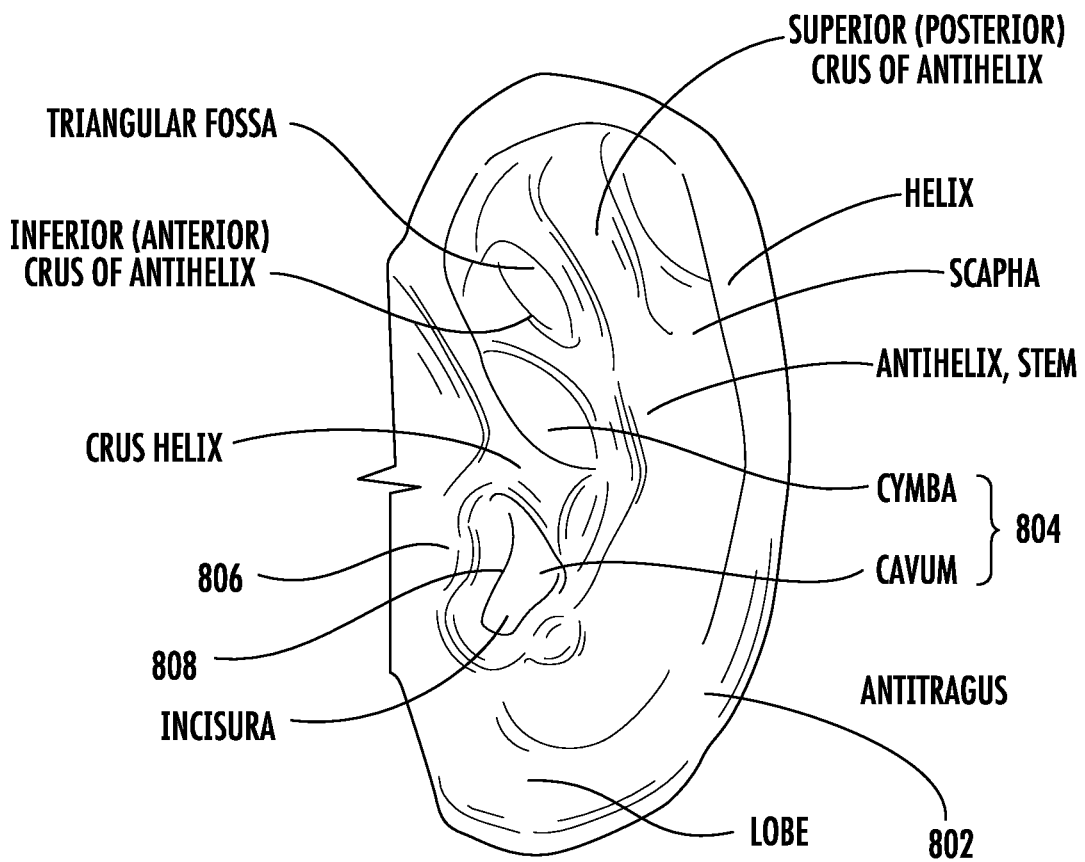
FIG. 8 is an exterior perspective view of a typical human ear, illustrating various anatomical features thereof.
Figure 9A:
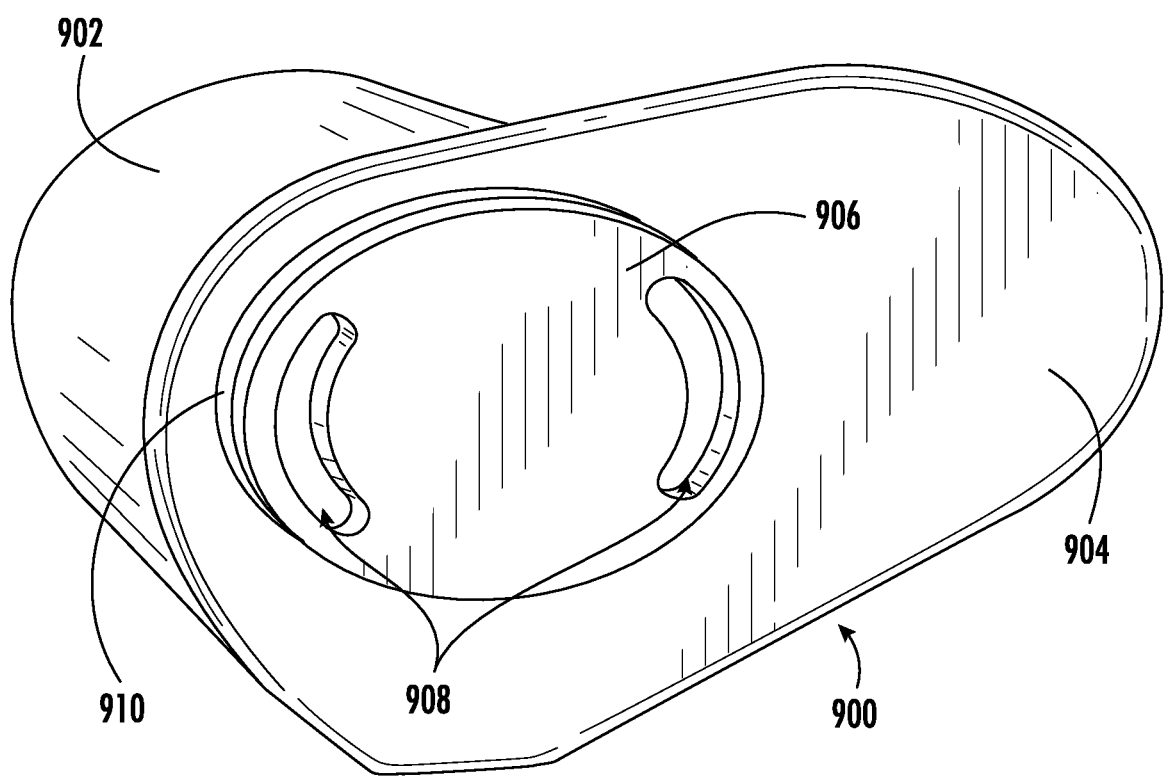
FIGS. 9A-9C are front perspective, side elevation, and front elevation views, respectively, of one embodiment of the ear apparatus of the present disclosure.
Figure 9B:
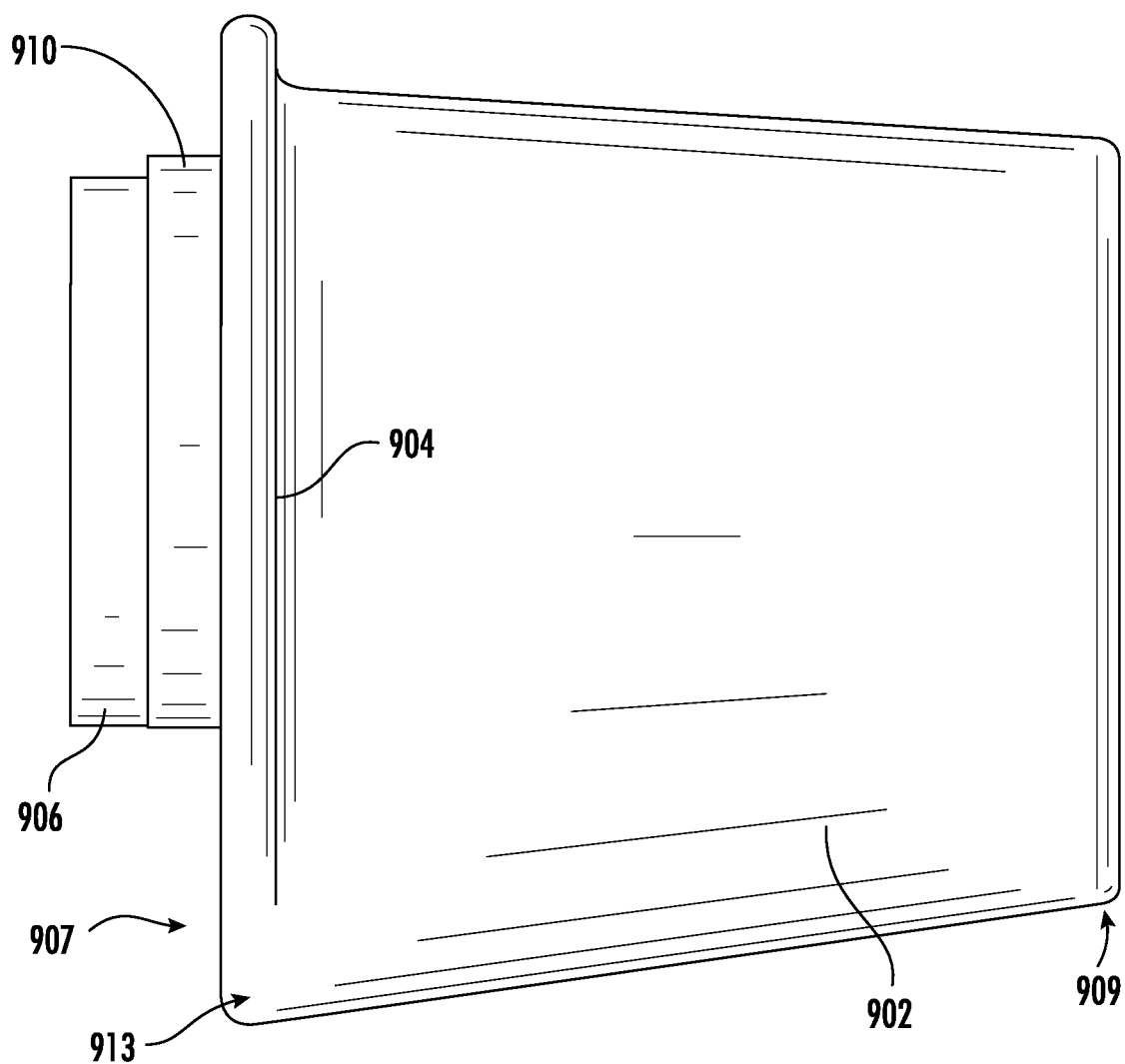
Figure 9C:
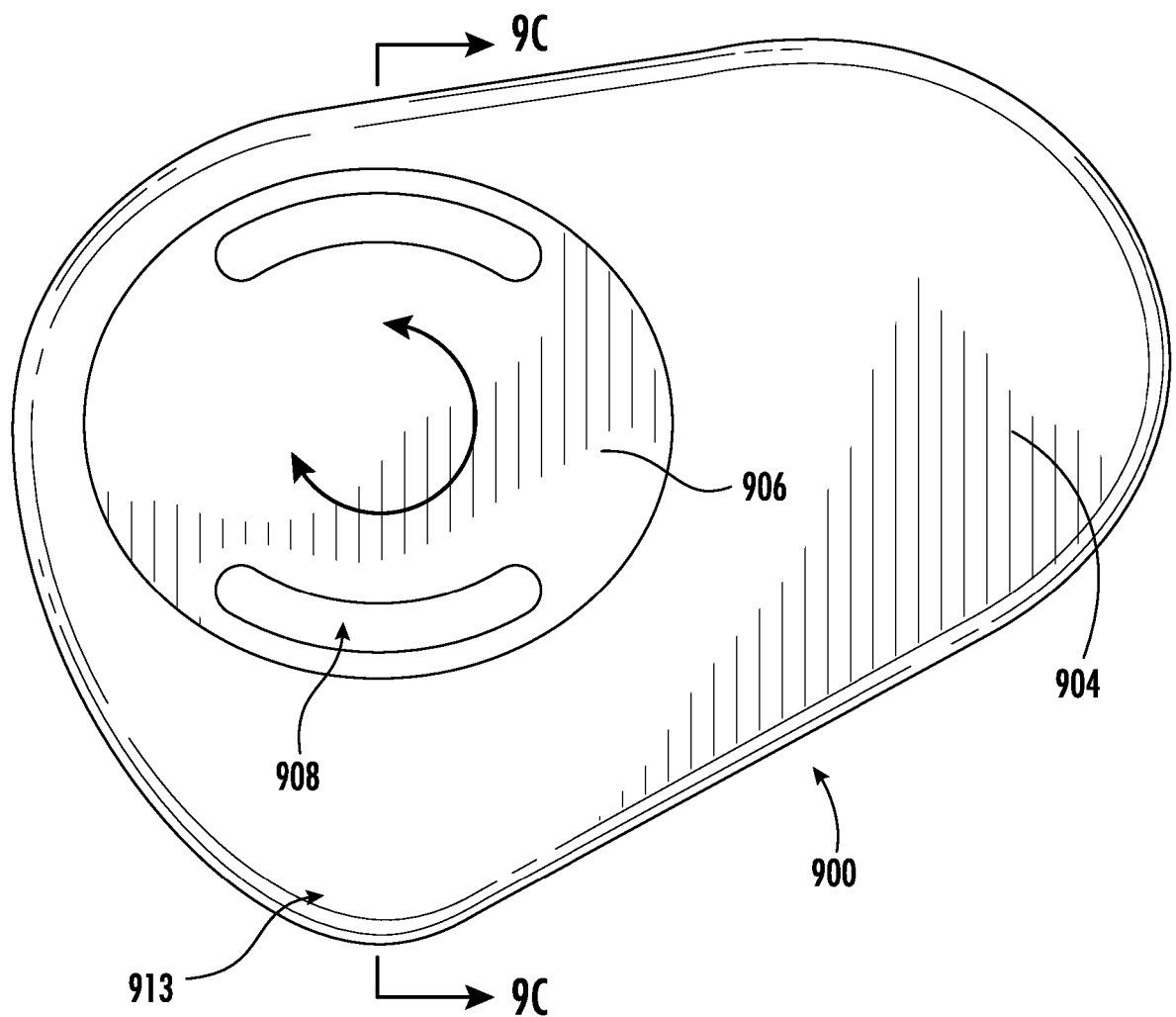
Figure 9D:
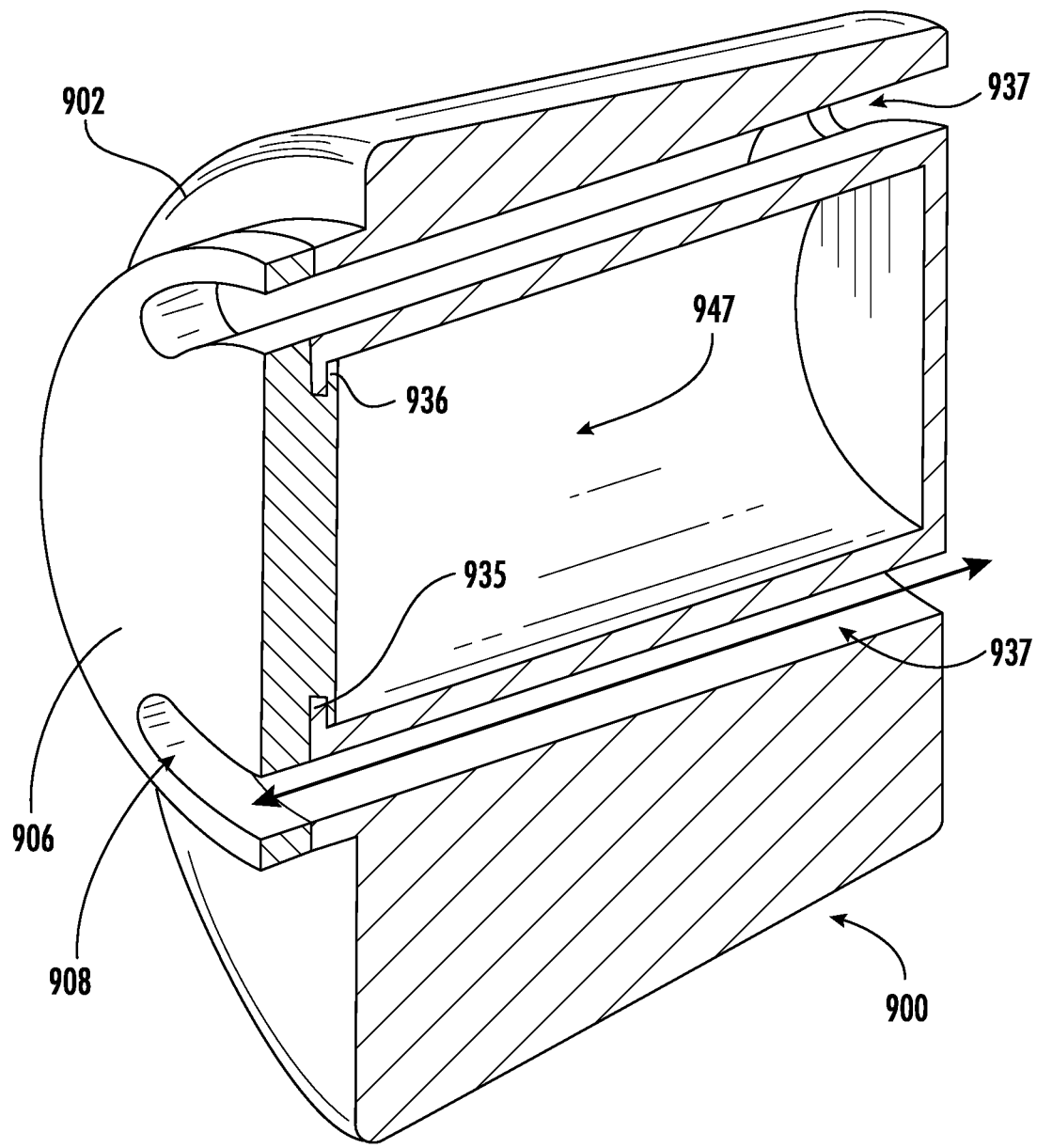
FIGS. 9D-9F are cross-sectional views of the ear apparatus of FIG. 9C, taken along line 9C-9C.
Figure 9E:
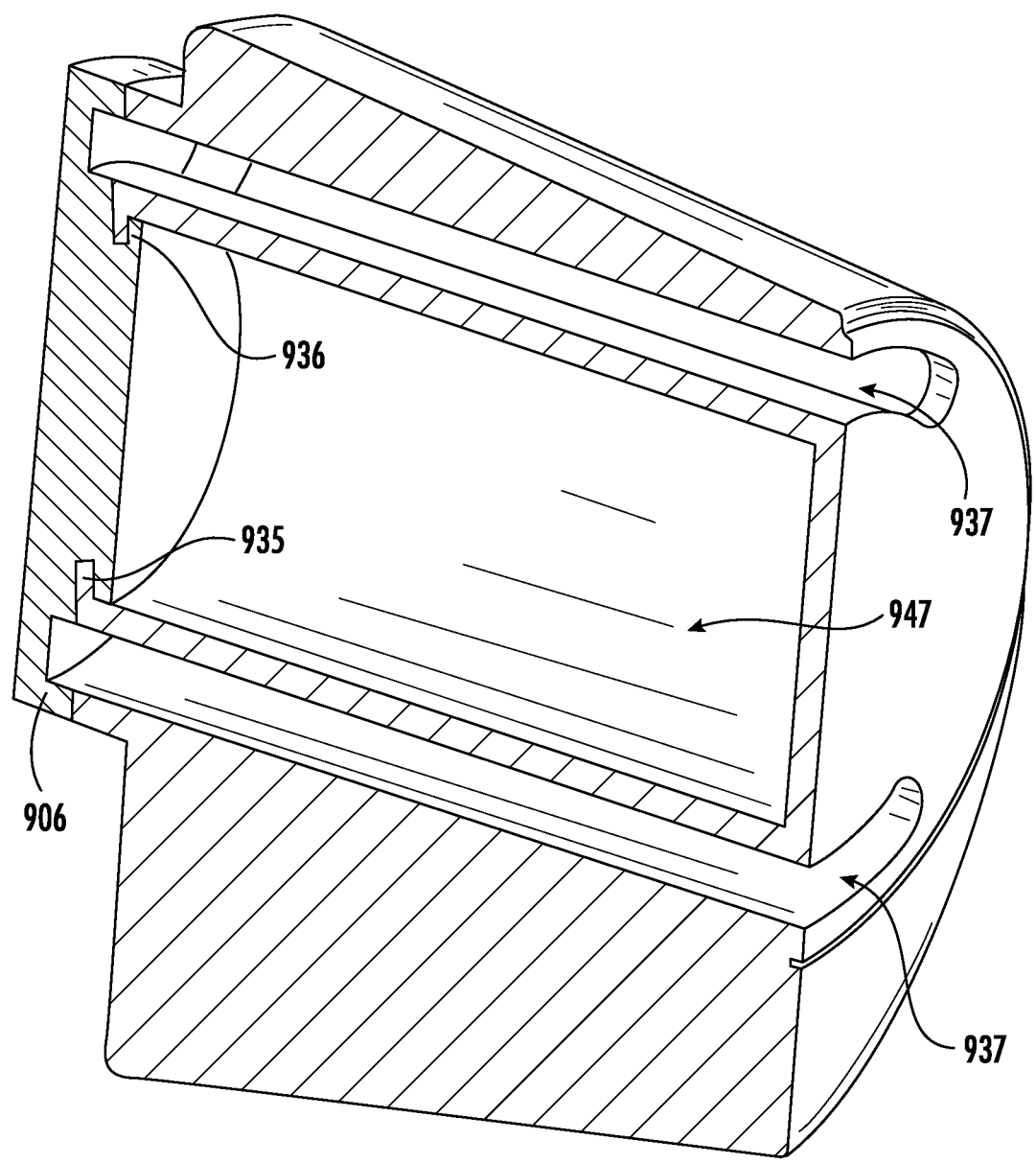
Figure 9F:
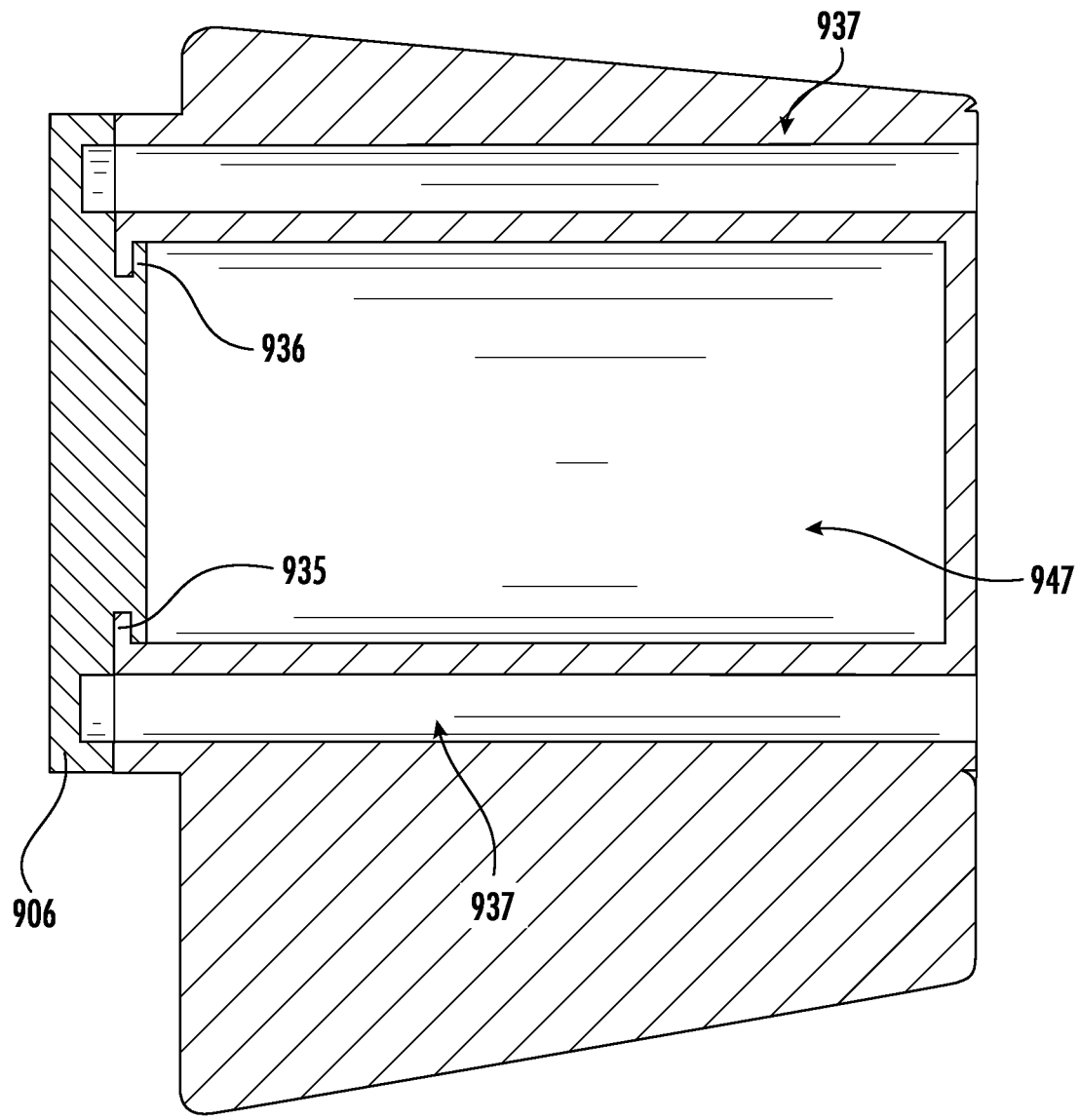

Referring now to FIG. 8, a typical human ear (viewed from a side perspective) is shown. In general, the ear includes the pinna (cartilage of outer ear) 802, and a path of entry from a lateral (outside) location to a medial (inside) location thereof. The outer or external portion of the ear includes a lateral aspect of the tragal cartilage ("tragus") 806, the concha 804 (including the cavum concha or conchal bowl), as well as the incisura inferiorly. In addition to the previous terms, within the outer ear canal, two new anatomical terms are introduced. The tragal "root" is defined as the anterior meatal wall adjacent to the medial surface of the tragal cartilage. The tragal "valve" is defined as a one centimeter cross-sectional area of the external auditory canal extending from the tragal root anteriorly to the conchal bowl posteriorly. Due to the flexible nature of this cartilage, the valve functions by exerting circumferential pressure to assist in the retention of the apparatus. Orientation of the apparatus in line with the incisura prevents rotation when the device is manually actuated. Using these landmarks, the apparatus sits firmly in the external cartilaginous ear canal avoiding discomfort from direct contact with the bony portion of the medial external auditory canal.

Description of Exemplary Embodiments

It is noted that while the apparatus of the disclosure described herein are discussed primarily with respect to use in a recreational context, such as by consumer, certain aspects of the disclosure may be useful in other applications, including, without limitation, non-recreational consumer use (e.g., in an office or work setting), in industrial applications (e.g., to selectively exclude noise, airborne contaminants, or the like); in commercial diving applications; in military, government or other applications (e.g., in aircraft, spacecraft, submersibles or submarines); in communications or entertainment applications/systems (e.g., personal media devices, consumer electronics, or automotive applications); and in medical or therapy applications (such as e.g., for protection of a ruptured eardrum or other compromised physiology).

It is also noted that while the ear apparatus of the disclosure is described herein primarily in the context of a human wearer or user, many of the principles and features of the disclosure are adaptable to other species and their particular anatomical features including, without limitation, primates such as e.g., chimpanzees.

Exemplary Apparatus—

Referring now to FIGS. 9A-9F, one embodiment of the ear apparatus of the present disclosure is shown and described.

As illustrated in FIGS. 9A-9F, the exemplary apparatus includes a roughly cylindrical body 902, an eccentric retention element 904 disposed on the outer or exterior end 907 of the body 902, and a valve assembly 906 disposed on the outer surface of the outer end, so that it can be manually actuated by the wearer when the apparatus 900 is inserted in the cartilaginous canal. Inferior to the body 902 is a substantially cylindrical barrel element 910 which is affixed within the body 902 such that an outer end of the barrel protrudes past the outer face of the retention element 904, and includes an interior cavity 947 and which is at least partly open on the interior end of the barrel 910.

The base (inferior) portion 913 of the body 902 is somewhat distended relative to the other radial portions of the body 902, such that the base portion 913 extends downward to engage the "conchal Incisura" as discussed below in greater detail.

Figure 5:
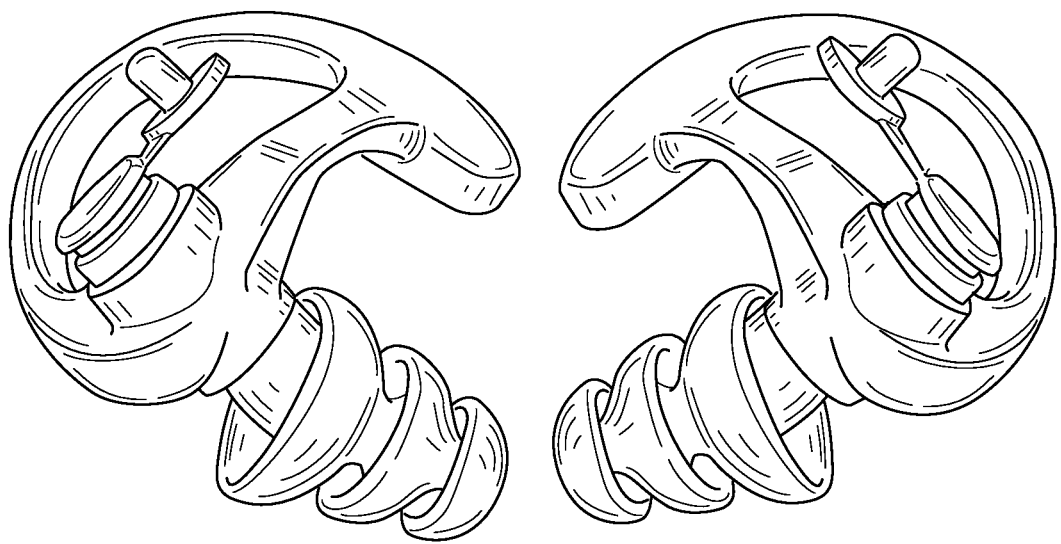
FIG. 5 is a perspective view of yet another variation of the "plug" type of protection device according to the prior art, which includes at least some selective sound attenuation capability.
Figure 6B:
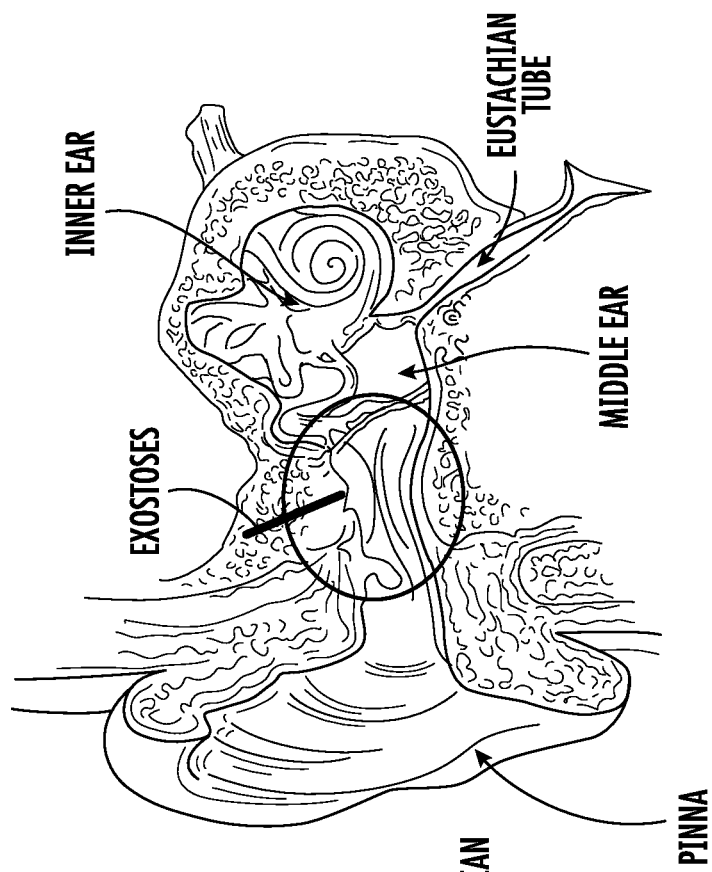
FIGS. 6A and 6B are illustrations of partial cross-sections of a typical human ear, both normal and after progression of exostosis, respectively.
Figure 6A:
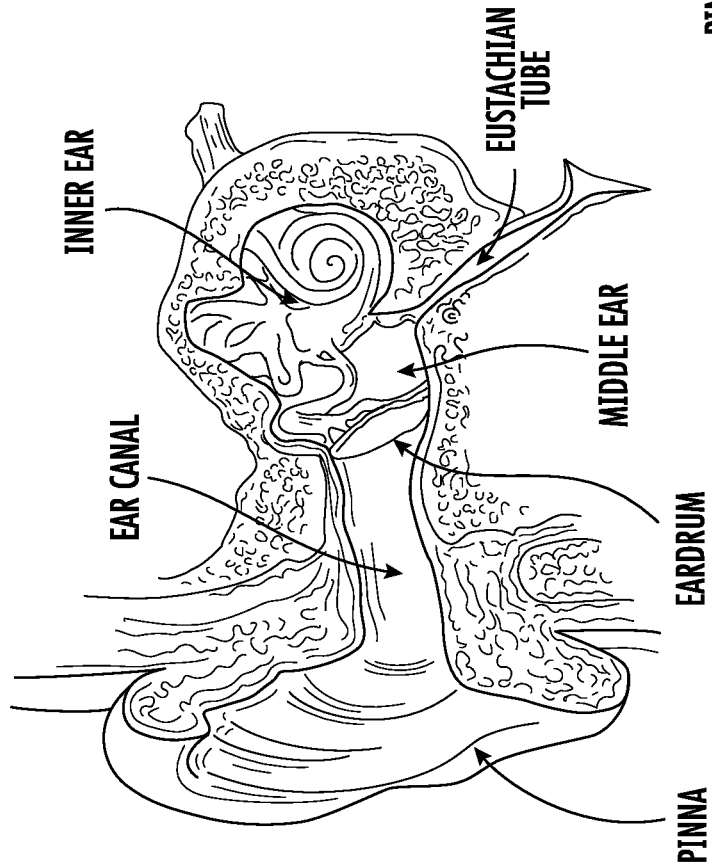
Figure 7A:
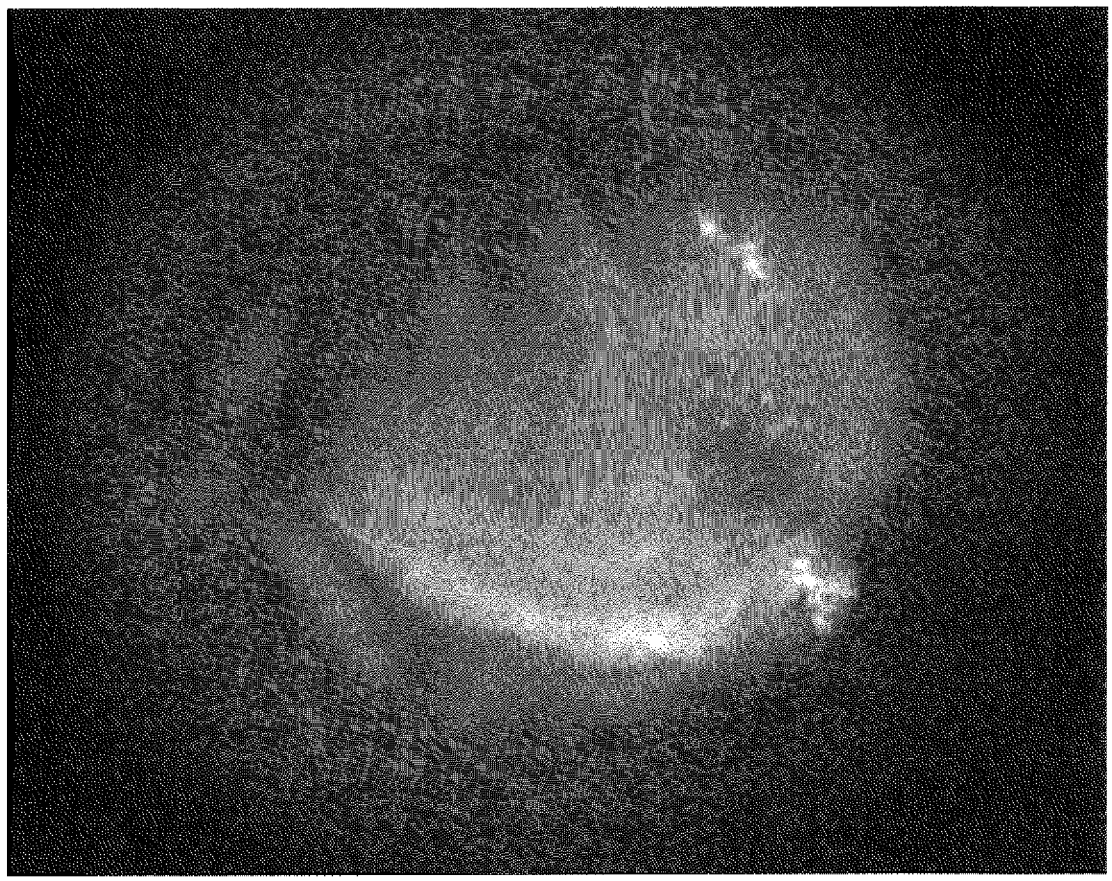
FIGS. 7A and 7B are microscopic images of a human ear, both normal and after progression of exostosis, respectively.
Figure 7B:
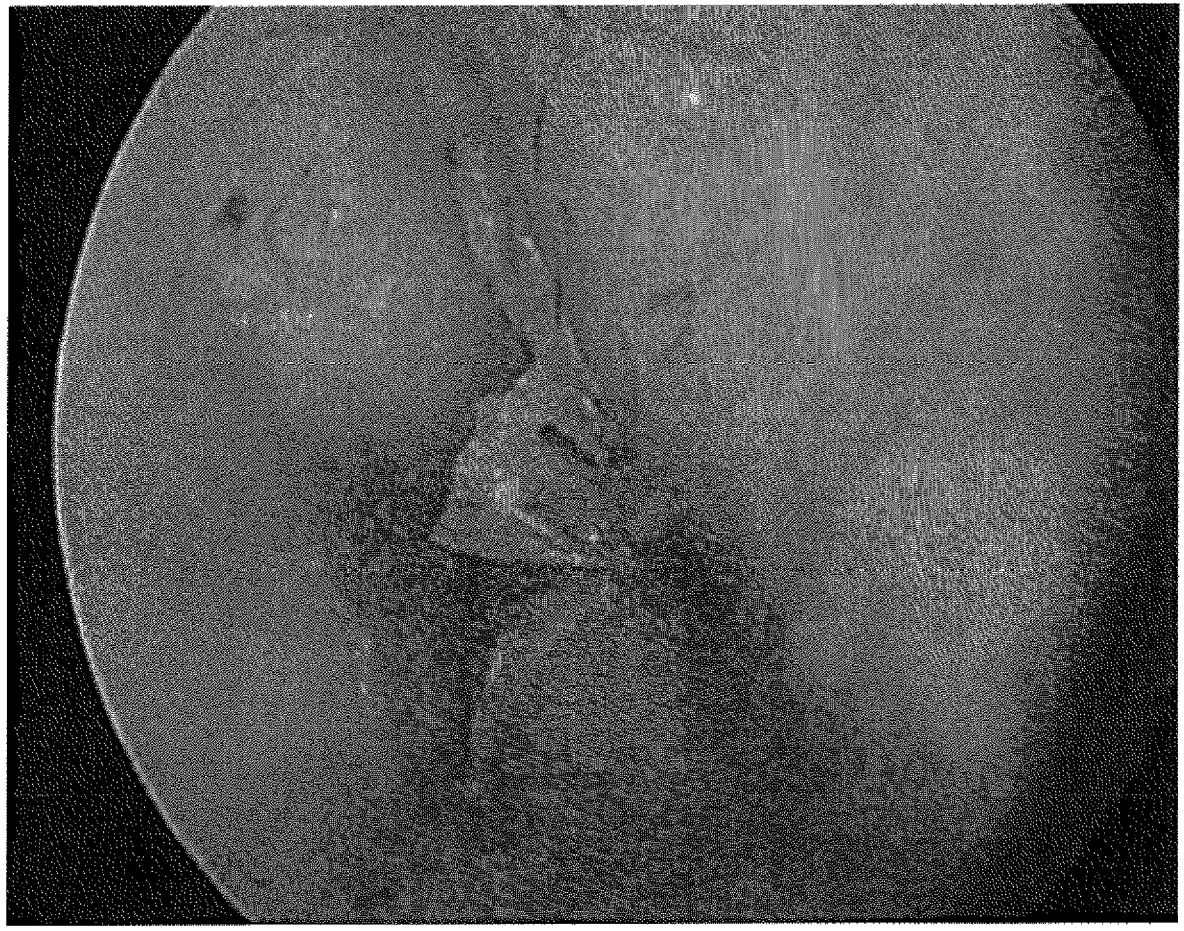

The valve assembly 906 is in the exemplary embodiment formed of a single-piece (e.g., molded polymer) stem 935 and plate (discussed in greater detail below with respect to FIG. 9D-9F) with two (2) apertures 908 formed in the plate as shown. The valve plate rotates around the stem axis (e.g., under force provided by the wearer's fingertip(s)), so as to align the two apertures 908 with correspondingly shaped and placed inner apertures 937 formed in the outer surface of the barrel element 910 (the latter into which the valve stem 935 is rotatably received and engages with corresponding lands 936); see FIGS. 9D-9F. Hence, when rotated in a first position (FIG. 9C), the valve apertures 908 and barrel apertures 937 are aligned, allowing passage of air, water, etc. between the outer surface of the plate and the interior cavity 947 (and hence the ear canal of the wearer). When placed in a second position (FIG. 9A), the apertures 908, 937 are completely non-aligned with those of the barrel 910, and hence no flow exists. Modulation between these two states (which, in the exemplary embodiment, are 90 degrees of rotation apart), such that partial flow of air, water, sound, etc. can pass through to the ear canal, is accomplished by rotating the plate to a position between the first and second positions. Herein lie two salient advantage of the illustrated configuration over the prior art (e.g., FIG. 5); i.e., (i) the ability to immediately change the state of the valve from one state to another (e.g., open to shut) in an intuitive fashion and without having to fumble to "find the hole" in which to insert a stopper, and (ii) the ability to just as easily modulate the degree of flow between the exterior and interior regions of the apparatus to an almost infinite number of different positions (in contrast with the two states of the plug of FIG. partially stopped and completely stopped).

It will be appreciated that while the body is shown as being generally cylindrical in shape with a taper inward (i.e., the diameter of the body decreases as the interior end 909 is approached) and an inferior or base distension 913, other configurations may be used as well (and as described in greater detail subsequently herein), including without limitation an inverse taper (i.e., diameter increasing as interior end approached), a more cylindrical shape (no taper), a contoured shape (e.g., one or more regions that vary in diameter or other shape parameters, including e.g., non-linear taper rates), and even asymmetric shapes (e.g., those asymmetric around a central axis of the body running from the interior end to the exterior end 907, so as to make use of similar or other anatomical features which may be present on the wearer.

The retention element 904 is of a particular, irregular shape (when viewed in plan) and includes an eccentric region 905 which is used to aid in retention of the apparatus 900 when inserted into the wearer's ear, as discussed below. The retention element 94 is generally planar in shape, the plane of which is generally perpendicular to a central axis of the barrel element 910; however, it will be appreciated that the relationship between the components may be varied based on, e.g., the particular attributes or features of the wearer (or a class of wearers, such as those with a particular anatomical feature that distinguishes them from others).

It will also be appreciated that the present disclosure likewise contemplates substantially customized apparatus 900 which are formed so as to be anatomically optimized for each user or class of users. Using e.g., well known three-dimensional (3D) optical or laser scanning apparatus (such as of the type used in conjunction with so-called "3D printers"), a 3D model of a given user's outer ear and outer canal can be obtained, and the molding or formation of the apparatus 900 (including e.g., its shape/rate of taper if any, relative angle between the retention element plane and the central axis of the barrel element 910, shape of the eccentric region 905 of the retention element 904, etc.) adjusted accordingly. In fact, since human beings are often somewhat asymmetric in terms of anatomical features (including ears), it is contemplated that a "left/right side" model can be used to customize plugs for each ear (and e.g., labeled or color coded so as to permit ready insertion into the appropriate ear). Moreover, the present disclosure contemplates purchase and manufacture of such plugs in bulk for each user or class of users, such as for disposable apparatus, thereby assuring that the user will have a ready supply of customized plugs, while taking advantage of manufacturing economies. In one such paradigm, a home or workplace user can simply utilize a hand-held scanner to scan an "earprint" of themselves, and send it to a remote entity via e.g., Internet so as to effectuate the order and production of the customized apparatus.

Returning to the eccentric portion 905 of the retention element 904, the eccentric shape is used in the illustrated embodiment to engage the inner posterior rim of the aforementioned conchal bowl when the apparatus 900 is inserted into the wearer's ear and the retention eccentric portion oriented appropriately (i.e., in a generally posterior direction from the ear canal cartilage). Specifically, the far end or tip of the eccentric portion 905 is substantially radiused and rounded in profile (although other profiles and/or textures may be used in this portion to facilitate prevention of slippage/movement) so as to "catch" in the rim of the bowl, thereby keeping the body 902 of the apparatus biased forward (i.e., in anterior direction) and engaged behind the tragus (the latter which exhibits some degree of inward bias or resilience against the outer end 907 of the apparatus body 902).

In use, the apparatus 900 advantageously leverages the natural cartilaginous anatomy of the external ear via, inter alia, the so-called "tragal valve" to maximize comfortable retention. The plug apparatus 900 sits in conchal bowl (cavum concha), such that the tragus is anterior (towards the front) of the plug, with the plug situated at the tragal root (i.e., far forward and behind the tragus). The interior end 909 of the apparatus 900, when fully inserted, sits in the cartilaginous canal, which is the outermost part of the ear canal. Hence, the apparatus, when fully inserted, seals by pressing up against the cartilage of the ear canal, and not the bone/tissue of the inner ear canal as in the prior art. The user accordingly feels none of discomfort that would be felt if the device were to press against the bone of the inner ear canal.

Moreover, in the exemplary embodiment, the superior or top portion of the body 902 of the apparatus that contacts the apex of the external auditory canal meatus, while the distended inferior or base portion 913 of the body 902 contacts the conchal incisura. On the outside (lateral) end 907, the body 902 contacts the interior surface of the tragus, the latter acting as somewhat of a "catch" to prevent the apparatus 900 from dislodging from the cartilage of the outer ear canal.

Yet further, in another embodiment, the helical rim of the ear is advantageously used in the retention of the apparatus 900 in the superior aspect (i.e., above the plug apparatus when properly inserted).

Hence, in concert: (i) the taper of the body, (ii) the bias or resilience of the tragus, (iii) the interaction between the base distended portion 913 and the conchal incisura, (iv) the interaction between the top (superior) portion of the apparatus 900 and the helical rim, and (v) the forward bias and "catch" of the eccentric portion 905 of the retention element in the rear end of the conchal bowl, cooperate to maintain the apparatus 900 firmly seated in the outer canal cartilage, and also prevent rotation (i.e., about the ear canal exist) or yaw (i.e., side-to-side rotation) of the apparatus 900 on the wearer. Herein lies yet another salient advantage of the exemplary apparatus 900 over the prior art; i.e., that it can be effectively retained in the ear, and perform its desired sealing function, without significant intrusion into the ear canal (and the attendant problems of discomfort associated therewith), and without undue outward (radial) bias due to compression. Simply stated, the apparatus 900 does not have to be heavily compressed and "wedged" deeply into the ear canal to be effective and to stay in place. This represents a wholly different paradigm than the prior art approaches discussed supra with respect to FIGS. 2-5.

In one exemplary implementation, at least some of the outer portion of the body 902 is made of an at least partly resilient material (e.g., an elastomer such as a silicone rubber-based compound or the like, or alternatively a "memory foam" such as PVC- or polyurethane-based compounds), such that the external or outer peripheral portion is at least partly compressible and resilient against the inner surfaces of the outer ear canal. This tends to aid retention of the plug 900 within the outer ear canal by, inter alia, increasing the surface area of contact between the outer surfaces of the plug and the surfaces of the outer ear canal, thereby providing enhanced friction and hence retention.

Other Embodiments and Features

Figure 10:
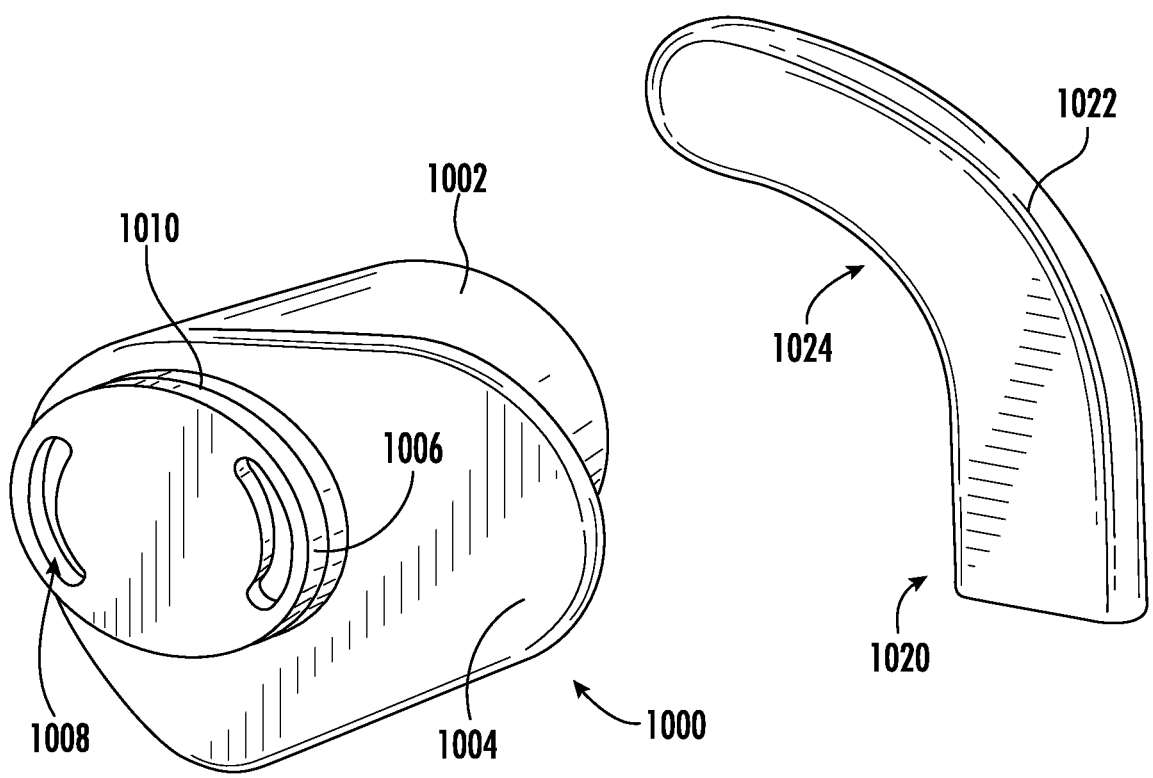
FIG. 10 is a front perspective view of another embodiment of the ear apparatus of the disclosure, including its complementary magnetic retention element.
Figure 10A:
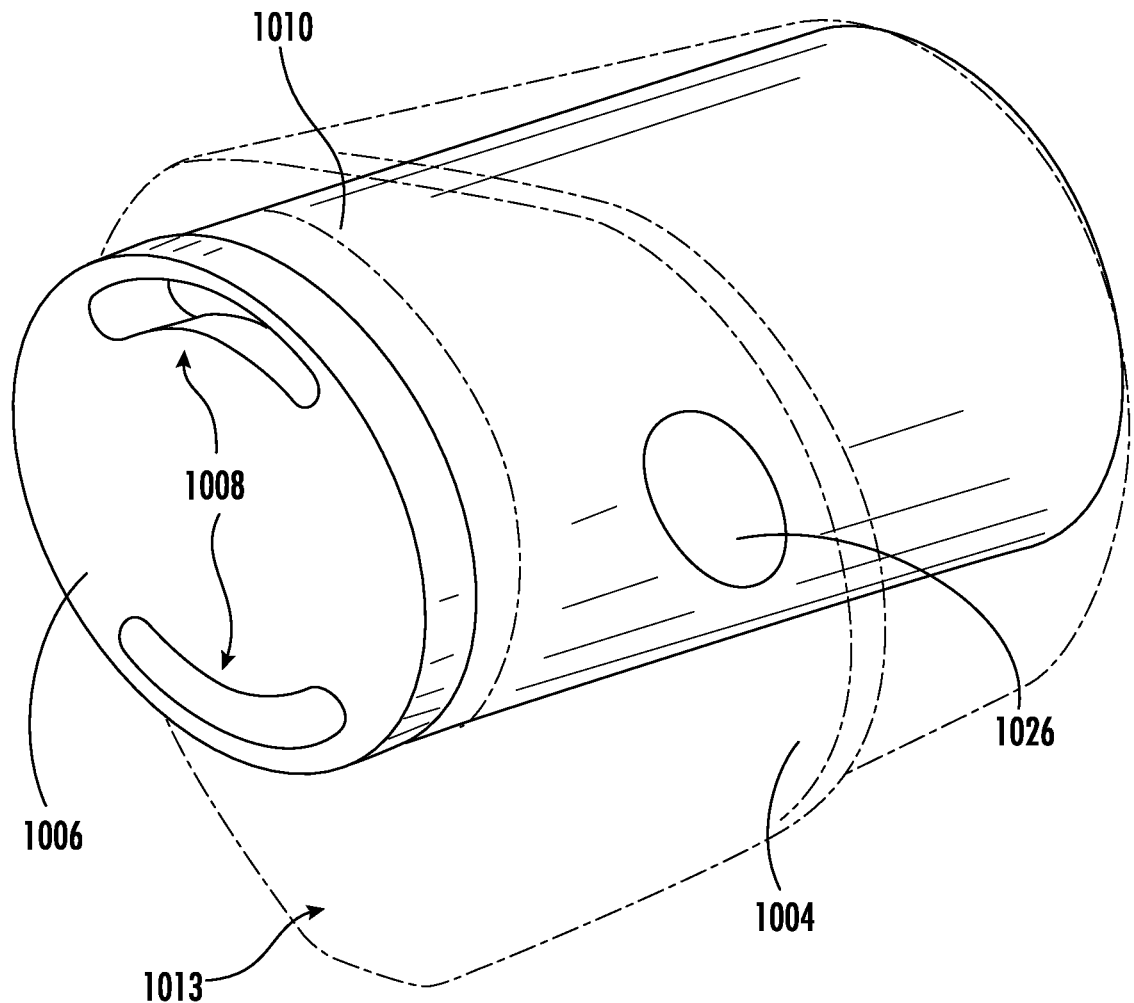
FIG. 10A is a front perspective transparency view of the ear apparatus of FIG. 10, illustrating exemplary placement of the magnetic element in the retention element thereof.

Referring now to FIGS. 10-10A, another embodiment of the ear apparatus of the present disclosure is shown and described. As illustrated, the apparatus 1000 of FIG. 10 is generally similar to that of FIGS. 9A-9F and includes a body 1002, retention element 1004, valve 1006 with apertures 1008, barrel 1010, and base region 1013, yet also includes a behind-ear retention bar 1020 which further aids in keeping the apparatus 1000 firmly retained in the wearer's ear. In the illustrated variant, a magnetic element 1026 is disposed within the retention element 1004 of the apparatus 1000, and the behind-ear bar 1020 also includes a complementary magnetic element (not shown) within the interior of the bar body 1022. The poles of the two magnetic elements are aligned such that a magnetic attraction between them is created, and the magnetic field permeates the wearer's ear cartilage. Thus, the bar 1020 placed behind the ear in effect "clamps" the retention element 1004 (and hence the ear apparatus 1000) in place. The shape of the behind-ear bar 1020 also includes an inner curved portion 1024 so as to rest on and accommodate the auricular groove portion of the ear cartilage where it joins the wearers head. The bar body 1022 includes magnetic material (e.g., ferrous material or the like capable of magnetization) over a portion of its length such that the placement of the bar need not be precise, and the relative positions of the bar 1020 and ear apparatus 1000 can change while still maintaining the magnetic attraction. The bar body 1022 is also sized and configured such that it does not present any significant discomfort to the user (i.e., is crafted so as to be lightweight and not bulky in terms of width or volume). Other configurations of the "bar" may be used consistent with the disclosure, including e.g., ovals, discs, and so forth; however, the bar shape has the advantage of being mechanically stable in that it sits atop the ear cartilage and behind the pinna and hence is somewhat less prone to falling off under e.g., vibration or shock.

In another variant of the ear apparatus, the apparatus includes a secondary (internal) valve assembly that is selectively (and passively) actuated or de-actuated via a thermally reactive material within at least a portion of the plug body. In one variant, the thermally operated valve is disposed within the cavity 947 of FIGS. 9D-9F, and acts as a safety mechanism or backup to the outer valve 906; i.e., in case the wearer inadvertently leaves the outer valve open, is caught unexpectedly, or the outer valve leaks-by significantly (i.e., cold water or cold air makes it into the cavity). In such cases, the thermally activated valve senses the cold air/water, and obstructs its orifice to as to prevent gross passage of cold water/air into the inner ear canal. In one implementation, the thermally activated valve utilizes a shape memory alloy (SMA) of the type known in the art. Shape memory alloy (SMA) generally consists of a metal that is capable of "remembering" or substantially reassuming a previous geometry or physical condition. For example, after it is deformed, it can either substantially regain its original geometry by itself during e.g., heating (i.e., the "one-way effect") or, at higher ambient temperatures, simply during unloading (so-called "pseudo-elasticity"). Some examples of shape memory alloys include nickel-titanium ("NiTi" or "Nitinol") alloys and copper-zinc-aluminum alloys. Hence, in one embodiment, the valve diaphragm or "shutter" is configured such that upon exposure to normal ambient temperature (and conducted body heat); e.g., 60-90F, the shutter of the valve remains open, while when exposed to much colder air or water (e.g., 40-50F), the shutter deforms to occlude an orifice or aperture formed on the interior end of the apparatus 900. Water is a particularly good conductor of heat energy, and hence such valves will generally react faster when exposed to water of a given temperature as compared to air. It is also appreciated that other techniques and/or materials for thermal-mechanical response can be used as well consistent with the disclosure, such as those exhibiting a phase change as a function of temperature (e.g., from liquid to solid as temperature decreases).

It will also be appreciated that such SMA materials are reactive to or can be actuated with (comparatively small) electrical current. Hence, the current disclosure contemplates use of such a small current (e.g., via a miniature Lithium Ion or similar battery of the type described elsewhere herein) to actuate the primary (which may be the only) valve 906. For example, in one variant, a battery is disposed in the cavity 947 (FIGS. 9D-9F), and the apparatus 900 further includes an electrical microswitch accessible to the user (e.g., under a waterproof flexible diaphragm disposed on the outer/exterior surface of the plug apparatus. The user deflects the diaphragm by pushing inward on it, which actuates the microswitch to pass a current from the battery to an SMA filament or other component to open or close the valve.

The aforementioned (primary) valve assembly 906 can be configured to be operated in any number of other ways as well. For example, in one variant, the valve is configured to be "push" operated, such as via an internal spring and latch mechanism; e.g., an inward bias or push on the outermost portion of the valve opens the valve to admits air/water, a subsequent inward push retracts the valve stem to a fractional (e.g., ½) open position, and a third push retracts the valve stem to the closed position. While requiring less manual dexterity than the implementation shown in FIGS. 9A-9F, the push-button approach also only provides the ability for a limited number of states, as compared with a much greater capability for "fine tuning" associated with the embodiment of FIGS. 9A-9F.

In another variant, a one way valve and pump can be used to increase pressure in a bladder, which affixes the device in the ear and controls air/water passage. An inward bias or push on the pump forces air through the one-way valve and traps it in the bladder. As the bladder expands from subsequent pumps, the outer bladder walls increasingly retain the device in the ear canal and block the passage of air/water. The valve allows for full adjustable settings between open and close with subsequent pumps.

In a further variant, the exterior material(s) of at least a portion of the outer plug apparatus body 902 is configured to aid in retention of the ear plug 900 within the outer ear canal. In one variant, the material comprises a plurality of synthetic "micro-setae" or bio-adhesives disposed on the outer surface of the plug body so as to enable the setae to interact with the surface of the dermis of the wearer's outer ear canal tissue, thereby further obviating generally undesirable outward bias pressures which can lead to irritation of such sensitive tissues. In one embodiment, these synthetic micro-setae comprise nano-scale "splits" at or near their ends, so as to enhance van der Waals forces to provide the required adhesion (i.e., so as to frustrate slippage or dislocation of the apparatus 900 when disposed in the ear canal). Such synthetic setae may use polymers such as polyimide, polypropylene and polydimethylsiloxane (PDMS) (flexible and easily fabricated), as well as Carbon Nanotubes (CNTs) (having a much larger possible length-to-diameter ratio than polymers, and which exhibit strength and flexibility, as well as desirable electrical properties). In one implementation, so-called "Gecksin™" PDMS-based fabric produced by the University of Massachusetts (Amherst) is utilized as an outer layer or coating of at least a portion of the body 902 of the apparatus 900 (and optionally portions of the retention element 904), so as to interact with the ear canal tissue as described above. See e.g., https://geckskin.umass.edu/, the contents of such website incorporated herein by reference in its entirety.

In another variant, a low-cost (consumable) adherent material such as that used in 3M™ Tegaderm™ film dressings can be used as a (partial) coating or layer for the outer portion of the body 902 to help in retention of the plug apparatus 900 in the wearer's outer ear canal. Advantageously, Tegaderm and similar film-type dressing materials leave little if any residue, are flexible, provide good adherence, and are easily removed. Such Tegaderm material is generally limited to one use, so this variant is used in conjunction with the low-cost (disposable) implementations described subsequently herein; however, the present disclosure does contemplate use of the Tegaderm or similar "single use" materials in a removable fashion with a non-disposable ear apparatus 900.

Figure 11:
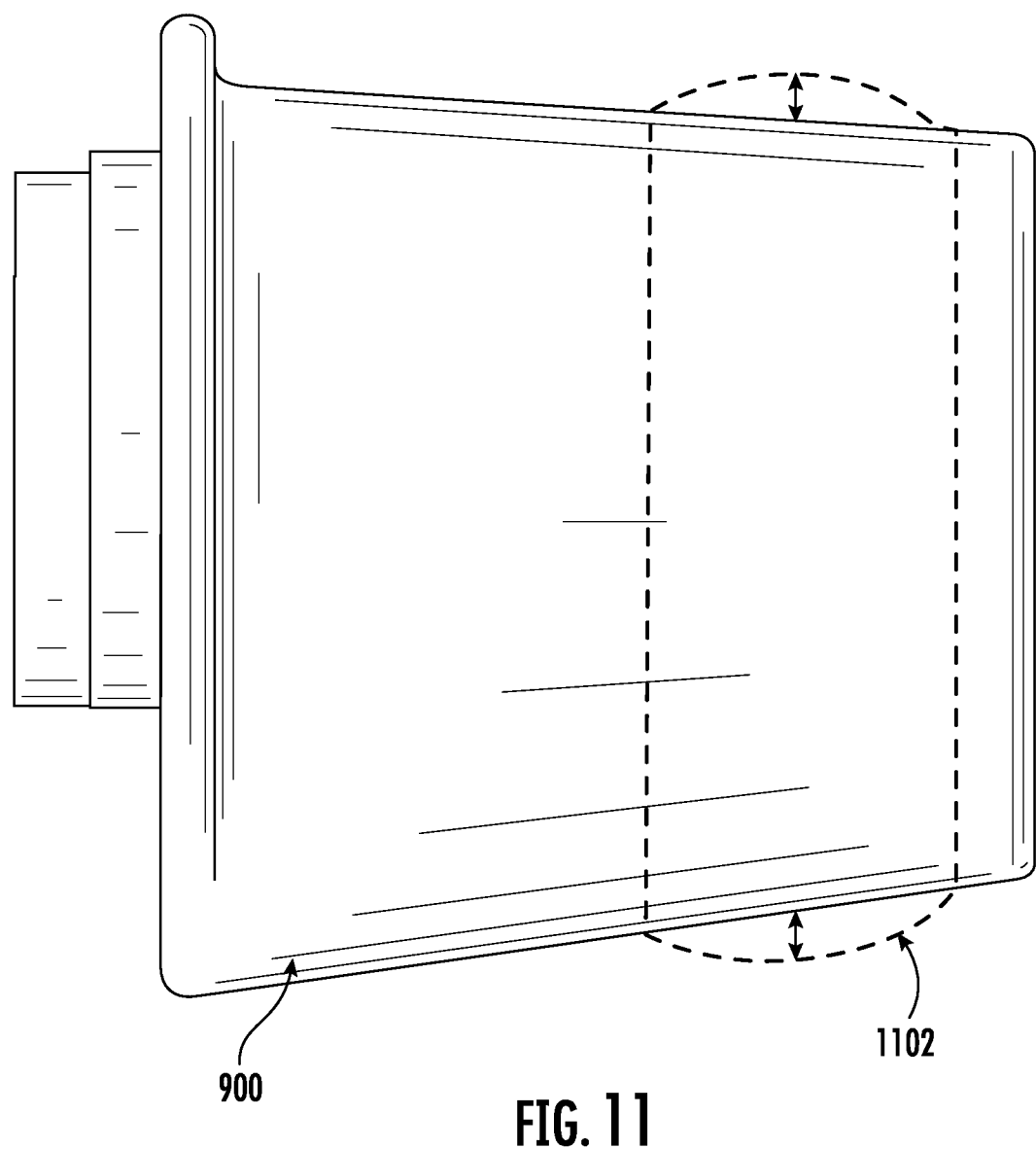
FIG. 11 is a side elevation view of another embodiment of the ear apparatus of the disclosure, wherein a resilient covering is used in conjunction with an internal radial bias member, the latter causing the apparatus to expand in one region radially, so as to accentuate retention in the user's ear.

In yet a further variant, the ear plug apparatus 900 is configured to be retained in place via an external mechanism (whether alone or in conjunction with the foregoing cooperation with the anatomical features of the wearer). In one implementation, the mechanism comprises an internal mechanism of the plug; e.g., a circumferentially expanding ring or region of the interior end 909 of the body 902 which contacts a portion of the inner surface of the outer portion of the ear canal, and which can be selectively actuated by the wearer. For example, the outer portion of the apparatus body 902 in that region can be made from an elastomeric or resilient material (e.g., a silicone rubber or the like), and a circumferentially expanding ring (i.e., in the cavity) biases the elastomer outward so as to "bulge" the outer surface of the body 902 in that which contacts a portion of the inner surface of the outer portion of the ear canal under interior spring assembly expansive force. See FIG. 11 herein. The expansion or "bulge" can be created using any number of different techniques, including e.g., vertical (i.e., along the central axis of the barrel 910) compression of a resilient of elastomeric material that causes its central region to bulge outward (akin to well-known prior art bottle stoppers or the like), thereby deflecting the resilient material of the outer body 902 of the apparatus to similarly bulge outward. The compression can be created via e.g., a mechanical actuator on the exterior end 907 of the plug apparatus 900, such as via a short lever, pushbutton arrangement, plunger (i.e., that can be pushed in or drawn out from the apparatus body 902) or the like.

Moreover, the resilient portion of the outer body 902 can be distended outward using e.g., air pressure. In one variant, a small toroidal or donut-like bladder is utilized within the apparatus cavity 947 (oriented collinearly with the aforementioned barrel element axis) such that it can be selectively inflated/deflated by the user, such as a small "pump" button on the exterior end 907 of the apparatus 900. In use, the wearer simply inserts the (deflated) plug 900 into their ear, and when properly positioned, pushes the pump button once or twice to inflate the bladder, and cause the outer (resilient) periphery of the body 902 to deflect as in FIG. 11. Deflation can be accomplished in one embodiment by simply holding the button inward for a short period of time (thereby allowing the comparatively higher pressure air to bleed out past the valve of the pump button).

In another embodiment, an external mechanism such as loop (e.g., disposed over the post auricular crease of the wearer's ear, as is common in hearing aids; not shown) can be used in conjunction with the apparatus 900 to exert an inward lateral force on the apparatus when disposed in the ear, thereby aiding retention. For instance, in one variant, the loop connects to the retention element 904 of the body 902, or another portion of the body 902, such that a substantially unitary assembly is made (the plug apparatus 900 optionally being detachable therefrom after removal).

Similarly, other exterior retention elements can be utilized consistent with the apparatus of FIGS. 9A-9D herein (and other embodiments described herein). For instance, a head band or "bridge" element can be utilized to connect the two (L/R) ear apparatus 900 to one another. Such band or bridge may be substantially rigid, resilient, flexible, and/or any other combination of desirable characteristics as dictated by a particular application. In an exemplary embodiment, the bridge is formed of a thin, lightweight yet highly resilient polymer such as polyethylene although other materials (polymeric or otherwise) may be used in combination or alone. Such resilient band exerts an inward lateral force on both of the ear plug apparatus 900 simultaneously when worn. It also provides the user with a mechanism to retain the individual plugs together as a pair, and also to conveniently retain the assembly around their neck when not in use. It will be appreciated, however, that other tethering mechanisms may be used consistent with the disclosure; e.g., a flexible polymer cord between the two plug apparatus, yet which does provide the inward force or bias as previously described.

Figures 12A, 12B:
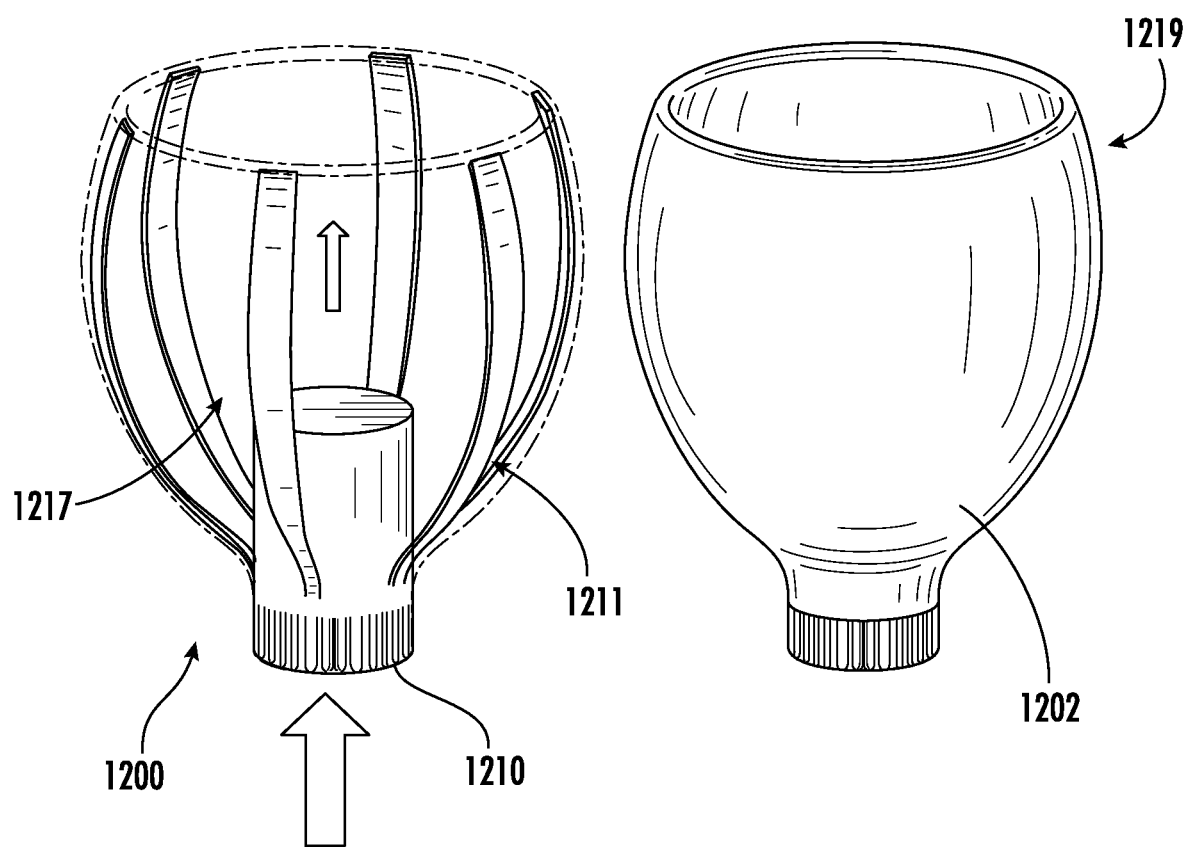
FIGS. 12A and 12B are partial transparency and side perspective views, respectively, of another embodiment of the ear apparatus of the present disclosure.

Referring now to FIGS. 12A and 12B, yet another embodiment of the ear apparatus is described. As shown, the apparatus 1200 generally includes a plurality of resilient fingers or strakes 1211 disposed generally peripheral to the interior end of the barrel element 1210. The barrel element 1210, as with the embodiment of FIGS. 9A-9F, includes the valve assembly (not shown) on its exterior end. Inside the barrel element resides the cavity 1217. The resilient fingers are formed of a resilient material (e.g., spring-grade steel or alloy, or polymer) and disposed such that when the user grasps the apparatus 1200 for insertion into the ear canal, they can depress the resilient fingers sufficiently so as to reduce the diameter of the plug at the interior end 1219 for insertion into the outer canal of the ear. Once inserted, the resilient fingers bias outward (under their own resilient bias or "springiness") against the inside of the outer ear canal, thereby tending to retain the apparatus 1200 in place. The outside of the exemplary apparatus (FIG. 12B) is covered in a sheet or membrane 1202 of resilient elastomer or polymer (e.g., silicone rubber) that maintains the integrity of the outer portion of the body (i.e., to exclude sound, air, water, etc.), yet which can expand and contract accordingly with the resilient finger movement. When the valve (not shown) is opened, air, water, etc. moves from the exterior to the interior of the apparatus 1200 in the direction shown. It will be appreciated that while a generally bowl-shaped contour for the resilient fingers 1211 and the outer membrane 1202, other shapes may be used consistent with the disclosure, so as to e.g., make maximal use of the various anatomical features, and maintain user comfort and wearability. For instance, a conical taper that is substantially parallel to that of the ear canal may be used. Alternatively, a negative or anti-taper (that is opposite that of the ear canal) could feasibly be used. Numerous other possible configurations exist.

While not shown, the apparatus of FIGS. 12A and 12B can also be used with other features or components described herein, such as inter cilia, the retention element 904 of FIGS. 9A-9F, the adhesive or micro-setae structures, etc.

In yet a further implementation, the plug apparatus 900 is sized and shaped so as to be retained generally in the desired place, but not provide a complete seal around its periphery with the surrounding ear tissue. Specifically, the plug is retained by the aforementioned anatomical features, yet is configured (e.g., by shortening its interior end 909, and/or enhancing its taper) to protrude less deeply into the outer ear canal (and hence require less compression of the tissue/cartilage in that region). This embodiment seeks only to mitigate cold water or air flow into the ear canal, and not completely prevent it, thereby maximizing comfort for the wearer during periods of extended use.

In still a further implementation, the ear plug apparatus 900 is made from low-cost materials and utilizes conventional manufacturing processes so as to render it disposable after as few as one use. For example, the outer body 902, valve 906, retention element 904, and barrel 910 can all be formed from low-cost injection-molded polymers, and/or elastomers, thereby reducing the cost of each apparatus 900 into a range where they can feasibly be used only once (or a few times), so as to e.g., maintain the sanitary nature thereof. The other portion of the apparatus may be coated or impregnated with anti-microbial materials to reduce the risk of ear infection in contaminated environments, if desired. These approaches can also be applied to various other configurations described herein; e.g., to that of FIGS. 12A and 12B, as well as others.

Figure 13:
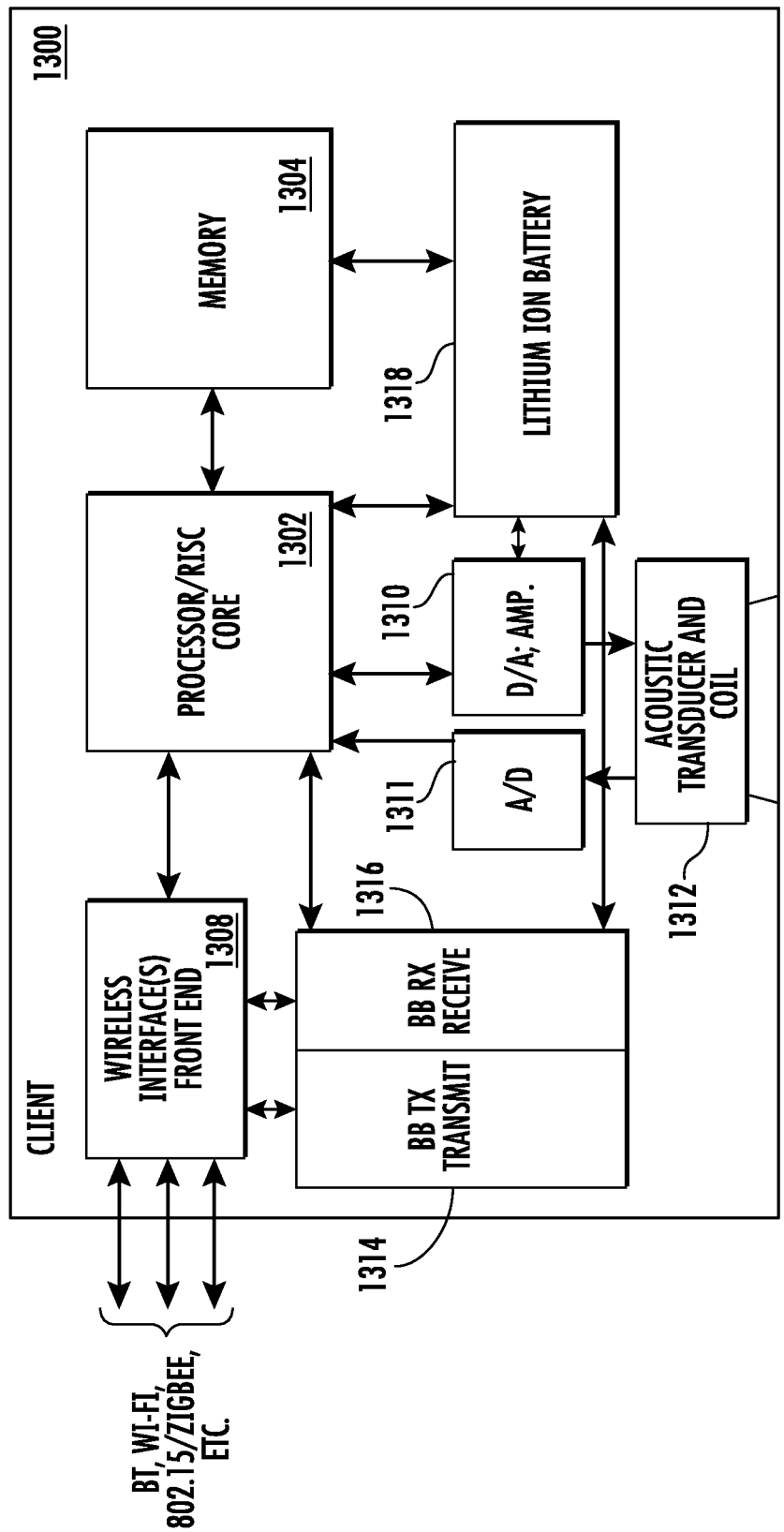
FIG. 13 is a functional block diagram of another exemplary embodiment of the ear apparatus according to the present disclosure, configured for one- or two-way communication.

In another aspect, electronic ear apparatus is disclosed. In one embodiment, the electronic apparatus includes an at least partly compliant (e.g., elastomeric) outer body, and an interior cavity configured to contain a plurality of electronic components. FIG. 13 illustrates a block diagram of one such apparatus 1300 according to the present disclosure. As shown, the apparatus 1300 includes, inter alia, a processor subsystem 1302, a memory module 1304, a power supply (e.g., Lithium ion battery) 1318, a digital to analog (D/A) converter and associated amplifier 1310; a microacoustic transducer module 1312, an analog-to-digital (A/D) converter 1311, one or more radio frequency (RF) front ends 1308, a transmit module 1314, and a receive module 1316.

In one exemplary embodiment, the processor apparatus 1302 may include one or more of a digital signal processor, microprocessor, field-programmable gate array, or plurality of processing components mounted on one or more substrates (e.g., printed circuit board). The processor subsystem 1302 may also comprise an internal cache memory. The processor subsystem is in communication with a memory subsystem 1304, the latter including memory which may for example comprise SRAM, flash, and/or SDRAM components. The memory subsystem may implement one or more of DMA-type hardware, so as to facilitate data accesses as is well known in the art. The memory subsystem of the exemplary embodiment contains computer-executable instructions which are executable by the processor subsystem.

In this and various embodiments, the processor subsystem 1302 is configured to execute at least one computer program stored in memory 1304 (e.g., a non-transitory computer readable storage medium). The computer program may include a plurality of computer readable instructions configured to perform various functions; e.g., audio or speech processing, decoding of encoded data (e.g., MP3 or similar files), filtering, noise or echo cancellation, decryption, data compression (e.g., via code excited linear prediction, LPC, or other such technique), as well as operations relating to the baseband of the wireless interface(s).

In one variant, the wireless transceiver includes a Bluetooth transceiver. The micro-acoustic assembly 1312 in one implementation comprises a small speaker and driving coil (and amplifier 1310) akin to those used in "ear buds", yet with reduced audio power capabilities so as to obviate electrical cords. A micro (e.g., small disc-shape, or flat planar and flexible) lithium ion battery 1318 is included in the cavity to power the electronic components and audio output. The battery can be recharged inductively, thereby obviating exposed electrical terminals. See e.g., http://www-.powerstream.com/thin-lithium-ion.htm, the contents of such website incorporated herein by reference in their entirety.

In another variant, the micro-acoustic assembly 1312 is configured to act as a transceiver; i.e., to operate as a speaker and vibrate an acoustic transducer under variations in voltage applied to the driving coil, and also act as a passive "microphone" to generate voltages via the coil when the transducer is vibrated by e.g., the wearer's voice while speaking. The A/D converter circuit 1311 receives the analog voltages from the transducer/coil, and converts them to the digital domain for further processing and transmission via the wireless interface. In one variant, the placement of the transducer of the assembly 1312 allows for bone conduction; e.g., where the wearer's jawbone meets the ear canal. Hence, the user's voice can be clearly perceived and converted to digital format without ambient noise, as in a traditional microphone.

In another variant, the electronic components include a Wi-Fi transceiver (e.g., Wi-Fi or Wi-Fi "Direct" enabled) as part of the radio frequency front-end 1308 and supporting components. It will be appreciated that Wi-Fi (and Bluetooth) radio transceiver integrated circuits have, as of the date of this filing, been commoditized to the extent that they are each readily available for less than one U.S. Dollar, ($1), thereby enabling their employment in limited-use or even disposable items such as earplugs.

In one variant, the Wi-Fi transceiver is configured to modulate its transmission power within the frequency band of interest to communicate only with very nearby Wi-Fi enabled devices (e.g., the user's smartphone or tablet when in their immediate possession or jacket pocket), so as to mitigate electromagnetic radiation (EMR) does to the wearer when in use. Notable, Bluetooth operating at e.g., 2.4 GHz does not suffer similar disabilities as traditional Wi-Fi transceivers, the latter designed to transmit over significantly greater ranges (i.e., WLAN vs. PAN).

In a further variant, an IEEE Std. 802.15 PAN-enabled integrated circuit device (e.g., Zigbee® or the like) is utilized within the cavity. Similar to the aforementioned 802.11 and Bluetooth wireless devices, ZigBee-enabled devices are generally commoditized, short-range devices capable of lower-bandwidth communications with nearby devices, such as a user's mobile device (e.g., smartphone or personal media device), PAN access nodes, etc. for at least one-way communication with the ear apparatus.

In another variant, the electronic apparatus is configured as a selectively actuated ear plug, and the plug(s) act as one or more "IoT" ("Internet of things") entities. For instance, the user's earplug apparatus can be configured to communicate with wireless home or premises automation apparatus, such as to activate the ear apparatus for music data streamed via a wireless transmitter within the home or premises upon occurrence of an event (e.g., the user "turning the home on" such as after arriving from work), or detection of other IoT-related device events (e.g., lights being turned on in a particular room, thereby ostensibly indicating the user's presence, or the stove being turned on, thereby indicating the user cooking dinner, or the spa being turned on, thereby indicating the user soaking therein).

Other events can also be fed to the ear apparatus via the aforementioned IoT or similar interface; e.g., the doorbell ringing, the premises (land line) or user's smartphone ringing, a security alarm sensor "beep" being transmitted when a door or window of the premises is open. The latter is particularly useful in the context of people living in noisy environments, and/or having a high degree of noise sensitivity. For instance, many people feel the need to sleep with ear plugs in (so as to block out e.g., road or vehicle noise, aircraft, etc.); one disability with this approach however is the user's lack of ability to detect events or noises which might indicate an emergency or safety-threatening situation; i.e., an intruder breaking a window, security system alert, loud "thumps", etc. The ear apparatus of the present disclosure overcomes such disabilities; for example, an IoT-enabled apparatus as described herein can be wirelessly coupled to the home's security system, a glass break sensor (common on security systems), a room sound monitor, a CO (carbon monoxide) or smoke detector, etc., so as provide a wireless "pass-through" for sounds or signals related to the user's premises or the like. It will also be appreciated that the ear apparatus of the present disclosure may be configured to include a miniature vibration unit (similar to that used on pagers or smartphones) which, upon actuation, causes a slight vibration of the ear apparatus, thereby ostensibly alerting the user of an IoT or other event. In one variant, different vibrational intensities and/or frequencies are used to signify different events; i.e., a low frequency/intensity for low-priority events, such as the phone ringing, and a higher intensity/frequency for e.g., actuation of a smoke detector, glass break sensor, etc. Analogously, different audible (acoustic) cues or signals can be utilized (whether alone or in conjunction with the vibrational cues) within the ear apparatus as well (e.g., a loud high-pitched tone for emergencies, a low-amplitude vibration for non-emergencies, etc.).

In another variant, the electronic apparatus is configured as a selectively actuated ear plug, and the plug(s) is configured to selectively turn on and off its transceiver (as well as other functions) as the valve is closed and opened, respectively. For example, one such implementation senses a rotational position of the valve 906 (i.e., absolute, or relative to another component's position) to determine a degree of actuation of the valve. The sensed position or state is used to selectively enable or disable various functions within the ear apparatus (or even wirelessly-communicative external devices, such as mobile user devices), including audio streaming or the aforementioned IoT-based alert functions. In one implementation, when the ear apparatus valve is sensed in the "open" position (e.g., via micro-potentiometer, micro-switch, or other means), it is presumed that no audio/alerts are needed or desired (i.e., the user can ostensibly hear through the ear apparatus apertures 908, 937), and hence all audio and communications are muted or ceased. Conversely, when the valve 906 is again shut, the aforementioned features are again enabled (e.g., unmated). Note that (i) the foregoing enablement/disablement can be binary, or alternatively modulated or varied (e.g., as a function of valve position); and/or (ii) the two ear apparatus of a given user may operate in independent (and heterogeneous) fashion, such as where one ear apparatus is closed (and hence the aforementioned audio, alert, etc. functions are enabled for that ear only), and the other at least partly opened (such that the user can hear ambient sounds). This feature is particularly useful, since many individuals, when wearing ear plugs or other hearing protection, often remove or actuate only a single one of the two devices; i.e., to hear out of one ear, for convenience.

In yet a further variant, the cavity 947 includes a miniature accelerometer in signal communication with a processor or microcontroller integrated circuit (e.g., ASIC). In one implementation, the accelerometer is used to sense the state of the wearer of the ear apparatus; e.g., ambulatory, awake but non-ambulatory, or asleep/unconscious. Such state determination can be used for e.g., gating of one or more functions of the ear apparatus, such as where audio streaming to the ear apparatus (and/or transmission from the ear apparatus, such as via the aforementioned jaw bone microphone, or biometric or telemetry signals such as temperature, heart rate, ambulatory status, etc) is only enabled when the user is ambulatory or waking/non-ambulatory. Likewise, IoT alerts or the like may only be generated (either audibly or via vibration) when the user is in the asleep/unconscious state). Exemplary MEMS-based micro-accelerometer apparatus useful with the present disclosure are described in, e.g., United States Patent Application Pub. No. 20130247669 to Swanson, et al. published Sep. 26, 2013 and entitled "Apparatus and Method for Providing an In-Plane Inertial Device with Integrated Clock", and Patent Application Pub. No 20140062567 to Waters, et al. published Mar. 6, 2014 and entitled "Auto-Ranging for Time Domain Extraction of Perturbations to Sinusoidal Oscillation", each of the foregoing incorporated herein by reference in its entirety, although it will be appreciated that the foregoing accelerometers are merely exemplary, and other types and/or configurations may be used consistent with the ear apparatus of the present disclosure.

Exemplary Methods—

To install the exemplary apparatus 900 in each ear, the user merely pushes the apparatus slightly at its interior end 909, and inserts the apparatus into the outer ear canal with the interior end 909 of the apparatus facing inward, and the retention element 904 oriented posterior and roughly level to the ground (i.e., an axis running through the retention element plane to the stem of the valve 906 oriented at roughly the "3 O'clock position for the left ear, or 9 O'clock position for the right ear, when the wearer is viewed from the side). The anterior portion of the body 902 is captured under the somewhat resilient tragus as previously discussed, and the lower or base portion 913 is captured by the conchal incisura portion of the conchal bowl. The distal tip of the retention element 904 is captured in the posterior portion of the conchal bowl, thereby securing the apparatus 900 within the wearer's ear. When positioned in the outer ear canal, the interior end 909 of the apparatus 900 expands somewhat (its compression having been released), and hence forms a seal around its periphery with the tissue and cartilage in that region.

Removal is generally the reverse of installation. The core is easily used for finger manipulation and removal.

In a further aspect, methods of treating a patient with an ear canal or ear drum condition or deficiency using the ear apparatus of the disclosure are now described. Specifically, in one embodiment, the method includes first installing the apparatus (e.g., that shown in FIGS. 9A-9F) which has a selectively variable aperture plug within the outer portion of the ear canal, so as to control the amount of sound, external contamination, or other deleterious substances or effects incident on the region. Next, the wearer or health care provider adjusts the valve 906 and hence variably covers the apertures within the apparatus body or barrel so as to permit a desired amount of air and sound to propagate through to the inner ear canal during normal wear (e.g., while the user is ambulating, sleeping, etc.). The aperture/valve is then re-adjusted so as to exclude moisture during e.g., showering or other situations where substantial water or water vapor is present, or exclude dust or other contaminants from the ear canal. Moreover, in patients with compromised ear drum (tympanic membrane), the valve can be adjusted to limit the amount of sound energy received within the canal, thereby avoiding acoustic trauma to the membrane. Advantageously, the wearer need to make multiple visits to the health care provider to adjust the valve to a desired/proper level; rather, they can simply do it themselves using e.g., the tip(s) of their finger(s). The "open cavity/barrel" configuration of the exemplary plug apparatus 900, along with the sizeable apertures 908 in the valve and the corresponding apertures in the barrel/body, enable a good volume of airflow into the inner ear canal, unlike prior art plugs discussed supra. Such enhanced airflow aids in healing of any compromised tissue, while still substantially protecting the ear canal and other internal components from trauma, contaminants, etc.

It should be recognized that while the foregoing discussion of the various aspects of the disclosure has described specific sequences of steps necessary to perform the methods of the present disclosure, other sequences of steps may be used depending on the particular application. Specifically, additional steps may be added, and other steps deleted as being optional. Furthermore, the order of performance of certain steps may be permuted, and/or performed in parallel with other steps. Hence, the specific methods disclosed herein are merely exemplary of the broader methods of the disclosure.

It will be further appreciated that while certain steps and aspects of the various methods and apparatus described herein may be performed by a human being, some of the disclosed aspects and individual methods and apparatus are generally computerized/computer-implemented. Computerized apparatus and methods are necessary to fully implement these aspects for any number of reasons including, without limitation, commercial viability, practicality, and even feasibility (i.e., certain steps/processes simply cannot be performed by a human being in any viable fashion).

While the above detailed description has shown, described, and pointed out novel features of the disclosure as applied to various embodiments, it will be understood that various omissions, substitutions, and changes in the form and details of the device or process illustrated may be made by those skilled in the art without departing from the disclosure. The described embodiments are to be considered in all respects only illustrative and not restrictive. The scope of the disclosure is, therefore, indicated by the appended claims rather than the foregoing description. All changes that come within the meaning and range of equivalence of the claims are embraced within their scope.

What is claimed is:

1. An apparatus for use on a living being, the apparatus comprising:
   a body, the body comprising a substantially tapered exterior shape and formed at least in part of an at least partly compliant material, the at least partial compliance and the substantially tapered exterior shape cooperating to enable the apparatus to be at least partially retained within an ear canal of the living being, the body further comprising at least one channel that connects to an interior surface of the body;
   first selectively actuatable apparatus configured to enable selective expansion and contraction of only a portion of the body in a direction transverse to a direction of insertion of the apparatus into the ear canal;
   a second selectively actuatable apparatus, the second selectively actuatable apparatus configured to variably occlude at least a portion of the at least one channel so as to variably control flow of at least one of air, sound waves, or water to the interior surface; and
   an inner cavity disposed within the body, the inner cavity comprising one or more electronic components, the one or more electronic components comprising:
      (i) processor apparatus;
      (ii) audio generation apparatus in data communication with the processor apparatus, the audio generation apparatus configured to transmit human-audible frequency signals; and
      (iii) a storage apparatus in data communication with the processor apparatus and having at least one computer program stored thereon, the at least one computer program comprising a plurality of instructions, which when executed, cause the processor apparatus to:
         receive a signal from the second selectively actuatable apparatus indicative of a position thereof; and
         based at least on the signal, selectively generate or not generate audio signals for transmission within the ear canal.

2. The apparatus of claim 1, wherein the second selectively actuatable apparatus comprises a substantially planar element, the substantially planar element being rotatable around an axis, the axis disposed substantially perpendicular to a plane of the substantially planar element.

3. The apparatus of claim 2, wherein the second selectively actuatable apparatus is configured to enable the living being using the apparatus to actuate the second selectively actuatable apparatus via the rotation of the substantially planar element.

4. The apparatus of claim 1, wherein the second selectively actuatable apparatus comprises a substantially planar element movably attached to an exterior surface of the body, the substantially planar element comprising at least one aperture configured to be:
   selectively aligned with the at least one channel in order to permit the flow of the at least one of the air, the sound waves, or the water from the exterior surface to the interior surface; and
   selectively misaligned with the at least one channel in order to limit the flow of the at least one of the air, the sound waves, or the water from the exterior surface to the interior surface.

5. The apparatus of claim 1, further comprising a retention element configured to be retained within a conchal bowl of the living being, the retention element comprising at least an anterior edge and a posterior edge, the anterior edge configured to at least partially abut a tragus of the living being, and the posterior edge configured to at least partially abut a posterior portion of a conchal incisura of the living being.

6. The apparatus of claim 1, wherein the substantially tapered exterior shape comprises a cross-section that decreases in circumference towards an interior, ear-drum facing portion of the apparatus.

7. The apparatus of claim 6, wherein the selective expansion and the contraction of only the portion of the body in the direction transverse to the direction of the insertion of the apparatus into the ear canal comprises an increase and decrease, respectively, of the circumference at a distal portion of the body, the distal portion disposed adjacent to the interior, ear-drum facing portion.

8. The apparatus of claim 1, wherein:
   the selective expansion and the contraction of only the portion of the body limits compression to ear canal tissue of the living being as a whole; and
   the substantially tapered exterior shape limits a depth of the insertion into the ear canal.

9. The apparatus of claim 1, wherein the signal indicative of the position comprises a signal indicating of a closed or occluded position, and the selective generation or non-generation comprises generation of the audio signals based on audio signals obtained from an environment external to the apparatus and the ear canal.

10. The apparatus of claim 1, wherein the one or more electronic components further comprise:
- a micro-acoustic assembly configured to operate as a transceiver and a passive microphone, the micro-acoustic assembly further configured to generate a plurality of voltages in response to receipt of a plurality of vibrations, the plurality of vibrations generated by the living being during speaking and conducted through at least a jawbone of the living being; and
- an A/D converter circuit configured to receive the plurality of voltages from the micro-acoustic assembly and convert the plurality of voltages to one or more digital signals.

11. An apparatus for use in an ear of a living being, the apparatus comprising:
- a body, the body comprising:
  - a retention element configured to be at least partly retained within a conchal bowl of the living being;
  - a substantially tapered portion configured to be at least partly retained within an ear canal of the living being, the substantially tapered portion configured to control an insertion depth of the apparatus into the ear canal of the living being; and
  - at least one channel connecting to an interior surface of the body; and
- a selectively actuatable valve apparatus, the selectively actuatable valve apparatus configured to, variably occlude at least a portion of the at least one channel so as to enable variable control of flow of at least one of water or air to the interior surface, the selectively actuatable valve apparatus configured to be automatically actuated based on detecting of a prescribed condition, the prescribed condition comprising a presence of at least water in a prescribed portion of the apparatus for use in the ear.

12. The apparatus of claim 11, wherein the selectively actuatable valve apparatus comprises a substantially planar element disposed at least partly on at least one exterior surface of the body, the substantially planar element being rotatable around an axis, the axis disposed substantially perpendicular to a plane of the substantially planar element.

13. The apparatus of claim 12, wherein the substantially planar element comprises at least one aperture configured to be:
- selectively aligned with the at least one channel in order to increase the flow of the at least one of the water or the air from the at least one exterior surface to the interior surface; and
- selectively misaligned with the at least one channel in order to decrease the flow of the at least one of the water or the air from the at least one exterior surface to the interior surface.

14. The apparatus of claim 11, wherein the retention element comprises at least an anterior edge and a posterior edge, the anterior edge configured to at least partially abut a tragus of the living being, and the posterior edge configured to at least partially abut a posterior portion of a conchal incisura of the living being, and the substantially tapered portion comprises an outer surface configured to circumferentially abut an interior wall of the ear canal and form a seal therebetween.

15. An apparatus for use in an ear of a living being, the apparatus comprising:
- a body, the body comprising:
  - a retention element configured to be at least partly retained within a conchal bowl of the living being;
  - a substantially tapered portion configured to be at least partly retained within an ear canal of the living being, the substantially tapered portion configured to control an insertion depth of the apparatus into the ear canal of the living being; and
  - at least one channel connecting to an interior surface of the body; and
- a selectively actuatable valve apparatus, the selectively actuatable valve apparatus configured to, variably occlude at least a portion of the at least one channel so as to enable variable control of flow of at least one of water or air to the interior surface, the selectively actuatable valve apparatus configured to be automatically actuated based on detecting of a prescribed condition, the prescribed condition comprising a temperature or change in temperature of the at least one of the water or the air in a prescribed portion of the apparatus for use in the ear.

16. The apparatus of claim 15, wherein:
- the substantially tapered portion is formed at least partly from a substantially compliant or flexible material such that when the apparatus is received within the ear canal, a cross-sectional shape of the substantially tapered portion complies with a shape of the ear canal to provide sealing against at least some of the at least one of the water or the air; and
- the substantially tapered portion is configured to, when the apparatus is received within the ear canal, limit a depth of insertion into the ear canal.

17. The apparatus of claim 15, wherein the selectively actuatable valve apparatus comprises a substantially planar element disposed at least partly on at least one exterior surface of the body, the substantially planar element being rotatable around an axis, the axis disposed substantially perpendicular to a plane of the substantially planar element.

18. The apparatus of claim 17, wherein the substantially planar element comprises at least one aperture configured to be:
- selectively aligned with the at least one channel in order to increase the flow of the at least one of the water or the air from the at least one exterior surface to the interior surface; and
- selectively misaligned with the at least one channel in order to decrease the flow of the at least one of the water or the air from the at least one exterior surface to the interior surface.

19. The apparatus of claim 15, wherein:
- the retention element comprises at least an anterior edge and a posterior edge, the anterior edge configured to at least partially abut a tragus of the living being, and the posterior edge configured to at least partially abut a posterior portion of a conchal incisura of the living being; and
- the substantially tapered portion comprises an outer surface configured to circumferentially abut an interior wall of the ear canal and form a seal therebetween.

20. The apparatus of claim 19, wherein the selectively actuatable valve apparatus further comprises an SMA (shape memory alloy) material configured to cause the automatic actuation.

* * * * *